(12) United States Patent
Mitra et al.

(10) Patent No.: US 6,252,140 B1
(45) Date of Patent: *Jun. 26, 2001

(54) PROMOTERS FROM CHLORELLA VIRUS GENES PROVIDING FOR EXPRESSION OF GENES IN PROKARYOTIC AND EUKARYOTIC HOSTS

(75) Inventors: Amitava Mitra; James L. Van Etten, both of Lincoln, NE (US)

(73) Assignee: Board of Regents, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/690,721

(22) Filed: Jul. 31, 1996

Related U.S. Application Data

(62) Division of application No. 08/268,072, filed on Jun. 27, 1994, now Pat. No. 5,563,328, which is a continuation of application No. 07/932,334, filed on Aug. 19, 1992, now abandoned.

(51) Int. Cl.[7] .......................... C12N 15/29; C12N 15/82; A01H 4/00; A01H 5/00

(52) U.S. Cl. .......................... 800/298; 800/295; 800/278; 435/419; 435/468; 435/320.1; 536/23.3; 536/24.1; 536/23.2

(58) Field of Search ................................. 800/200, 203, 800/250, 295, 278, 298; 435/172.3, 320.1, 419, 468; 536/23.2, 24.1

(56) References Cited

U.S. PATENT DOCUMENTS

| | | |
|---|---|---|
| 5,034,323 | 7/1991 | Jorgensen, et al. . |
| 5,085,588 | 2/1992 | Long et al. . |
| 5,097,025 | 3/1992 | Benfey et al. . |
| 5,563,328 * | 10/1996 | Mitra et al. .......................... 800/250 |

FOREIGN PATENT DOCUMENTS

| | | |
|---|---|---|
| 0 108 580 A1 | 5/1984 | (EP) . |
| 0 190 676 A1 | 1/1986 | (EP) . |
| 0 412 006 A1 | 2/1991 | (EP) . |
| 0 426 641 A2 | 5/1991 | (EP) . |
| WO 91/13994 | 3/1991 | (WO) . |

OTHER PUBLICATIONS

Rohe et al. Phytopathology. vol. 81, No. 10. p. 1246, Oct. 1991.*

An, et al., "Binary Ti Vectors for Plant Transformation and Promoter Analysis", 1987, 292, Methods in Enzymology, 153.

An, "A Potential Z–DNA–Forming Sequence is an Essential Upstream Element of a Plant Promoter", 1987, 211–214, Bioessays, 7.

de Bruijn, et al., "The Use of Transpos on Tn5 Mutagenesis in the Rapid Generation of Correlated Physical and Genetic Maps of DNA Segments Cloned into Multicopy Plasmids", 1984, 131, Gene, 27.

Griton, et al., "Restriction Site Map of the Chlorella Virus PBCV–1 Genome", 1987, 247–257, Plant Mol. Biol., 9.

Gorman, et al., "Recombinant Genomes Which Express Chloramphenicol Acetyltransferase in Mammalian Cells", 1982, 1044–1052, Mol. Cell Biol., 2.

Grabherr, et al., "The DNA Polymerase Gene from Chlorella Viruses PBCV–1 and NY–2A Contains an with Nuclear Splicing Sequences[1,2]", 1992, 721–731, Virology, 188.

Graves, et al., "Characterization of the Gene Encoding the Most Abundant in vitro Translation Product from Virus–Infected Chlorella–like Algae", 1992, 149–155, Gene, 113.

Ha, et al., "Identification of Upstream Regulatory Elements Involved in the Developmental Expression of the *Arabidopsis thaliana* cbl Gene", 1988, 8017, PNAS, 85.

Herman, et al., "An Expression Selection Vector to Isolate DNA Segments with Plant Promoter Activity", 1986, B24, Internal. de Physiol et de Biochimie, 94.

Jarvis, et al., "Transient Expression of Firefly Luciferase in Protoplasts of the Green Alga Chlorella Ellipsoidea", 1991, 317–321, Current Genetics, 19.

Lam, et al., "Site–specific Mutations Alter in vitro Factor binding and Change Promoter Expression Pattern in Transgenic Plants", 1989, 7890, PNAS, 86.

Liang, et al., "Direct Generation of Wheat Haploids via Another Culture", 1987, 336, Crop Sci., 27.

Mann, et al., "Cloning of Restriction and Modification Genes in *E. coli*: The HhaII System from *Haemophilus haemolyticus*", 1978, 97–112, Gene, 3.

Mitra, et al., "Three Distinct Regulatory Elements Comprise the Upstream Promoter Region of the Nopaline Synthase Gene", 1989, 294–299, Molecular Gen. Genetic, 215.

Narva, et al., Molecular Cloning and Characterization of the Gene Encoding the DNA Methyltransferase, M.CviBIII, from Chlorella Virus NC–1A, 1987, 9807–9823, Nucleic Acids Res., 15.

Rohe, et al., "Functional Analysis of a Chlorella Virus Adenine Methyl Transferase Gene Promoter in Agrobacterium and Plant Cells", 1991, 1246, Phytopathology, 81(10).

Schuster, et al., "Infection of a Chlorella–like Alga with the virus PBCV–1: Transcriptional Studies", 1986, 181–189, Virology, 148.

(List continued on next page.)

Primary Examiner—Lynette R. F. Smith
Assistant Examiner—Thomas Haas
(74) Attorney, Agent, or Firm—Suiter & Associates PC

(57) ABSTRACT

The invention is directed to novel promoters or mutants thereof from Chlorella virus DNA methyltransferase genes. A Chlorella virus gene promoter is operably linked to a first and/or second DNA sequence encoding a gene that is different from the Chlorella virus gene to form an expression cassette. An expression cassette can be introduced into prokaryotic and/or eukaryotic cells and can provide for a high level of expression of the gene encoded by the first and/or second DNA sequence. The invention also provides a method for screening other Chlorella virus genes for promoters that can function to express a heterologous gene in prokaryotic and/or eukaryotic hosts.

49 Claims, 3 Drawing Sheets

OTHER PUBLICATIONS

Schuster, et al., "Transcription and Sequence Studies of a 4.3–kbp Fragment from a ds–DNA Eukaryotic Algal Virus", 1990, 515–523.

Shields, et al., "Cloning and sequencing the cytosine Methyltransferase Gene M. cviJI from Chlorella Virus IL–3A[1,2]", 1990, 16–24, Virology, 176.

Stefan, et al., Molecular Cloning and Characterization of the Gene Encoding the Adenine Methyltransferase M. CviRI from Chlorella Virus XZ–6E, 1991, 307–311, Nucleic Acides Res., 19.

Van Etten, et al., "Chlorella Algal Viruses", 1991, 337–347, Microb. Rev., 55.

Van Etten, et al., "Viruses and Virus–like Particles o Eukaryotic Algae", 1991, 586–620, Microb. Rev., 55.

Velten, et al., "Selection–Expression Plasmid Vectors for use in Plants", 1985, Abstract Nº 1816, at p. 263, Plant Genetics.

Yanisch–Perron, et al., "Improved M13 Phage Cloning Vectors and Host Strains: Nucleotide Sequences of the M13mp18 and pUC19 Vectors", 1985, 103–119, Gene, 33.

Zhang, et al., "A Single Amino Acid Change Restores DNA Cytosine Methyltransferase Activity in a Cloned Chlorella Virus Pseudogene", 1992, 1637–1642, Nucleic Acid Res., 20.

Angenon, et al., "Expression of dicistronic Transcriptional Unites in Transgenic Tobacco", Dec., 1989, 5676–5684, Molecular and Cellular Biology., 9.

Frey, et al., "A Bacteriphage T4 Expression Cassette that Functions Efficiently in a Wide Range of Gram–negative Bacteria", 1988, 237–247, Gene, 62.

Hooykaas, et al., "Agrbacterium and Plant Genetic Engineering", 1992, 15–38, Plant Molecular Biology, 19.

Potrykus, "Gene Transfer to Cereals: An Assessment", 1990, 535–542, Bio/Technology, 8.

Sambrook, et al., "Molecular Cloning: A Laboratory Manual, 2nd Edition", 1989, 16.9 and 16.11, Cold Spring Harbor Laboratory Press.

Walden, et al., "Techniques in Plant Molecular Biology— Progress and Problems", 1990, 563–576, Eur. J. Biochem, 192.

Mitra, et al., "The Chlorella virus Adenine Methyltransferase Gene Promoter is a Strong Promoter in Plants", May 17, 1994, 1–9, Dept. of Plant Pathology & Cntr for Biotechnology, Univ. of Lincoln, NE.

Shields, et al., "Molecular Cloning and Characterization of the Gene Encoding the Cytosine Methyltransferase, M.CviJI, From Chlorella Virus IL–3A", 1989, Journal Cell Biochemistry, 13D:214.

Mitra, et al., "A Chlorella Virus Gene Promoter Functions as a Strong Promoter Both in Plants and Bacteria", Oct. 14, 1994, 187–194, Biochemical & Biophysical Research Communications, 204(1).

Mitra, et al., "Structural and Functional Analyses of *Arabidopsis thaliana* Chlorophyll a/b–binding Protein (cab) Promoters", Sep. 12, 1988, 169–179, Plant Molecular Biology, 12.

An, et al., "functional Analysis of the 3' Control Region of the Potato Wound–Inducible Proteinase Inhibitor II Gene", Jan. 1989, 115–122, The Plant Cell, 1.

Horsch, et al., "Inheritance of Functional Foreign Genes in Plants", Feb., 1984, 496–498, Science, 223.

Miwa, et al., "Kinetic Isotope Effects and 'Metabolic Switching' in Cytochrome P450–Catalyzed Reactions", Nov., 1987, 215–219, BioEssays, 7:6.

An, "Development of Plant Promoter Expression Vectors and Their Use for Analysis of Differential Activity of Nopaline Synthase, Promoter in Transformed Tobacco Cells", 1986,86–91,Plant Physiol, 81.

Gordon–Kamm, et al., "Transformation of Maize Cells and Regeneration of Fertile Transgenic Plants", 1990, 603–618, The Plant Cell, 2.

Shimamoto, et al., "Fertile TransgenicRice Plants Regenerated from Transformed Protoplasts", 1989, 274–276, Letters to Nature, 338.

Vasil, et al., "Herbicide Resistant Fertile Transgenic Wheat Plants Obtained by Microprojectile Bombardment of Regnerable Embryogenic Callus", Jun., 1992, 667–674, Bio/Technology, 10.

* cited by examiner

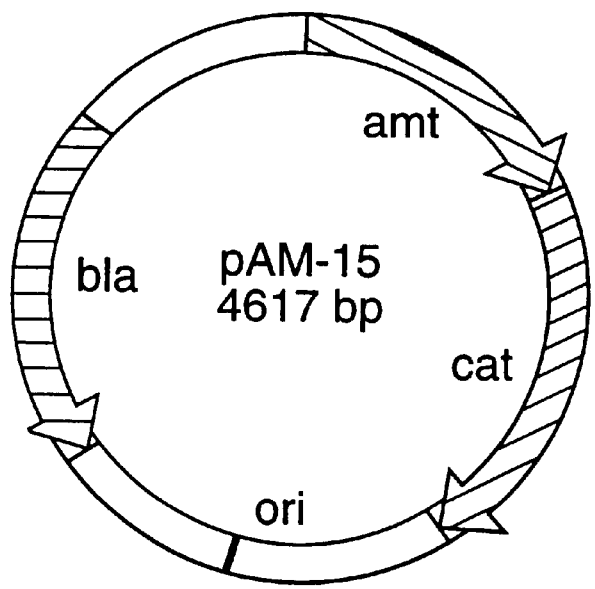
FIG. 1-A
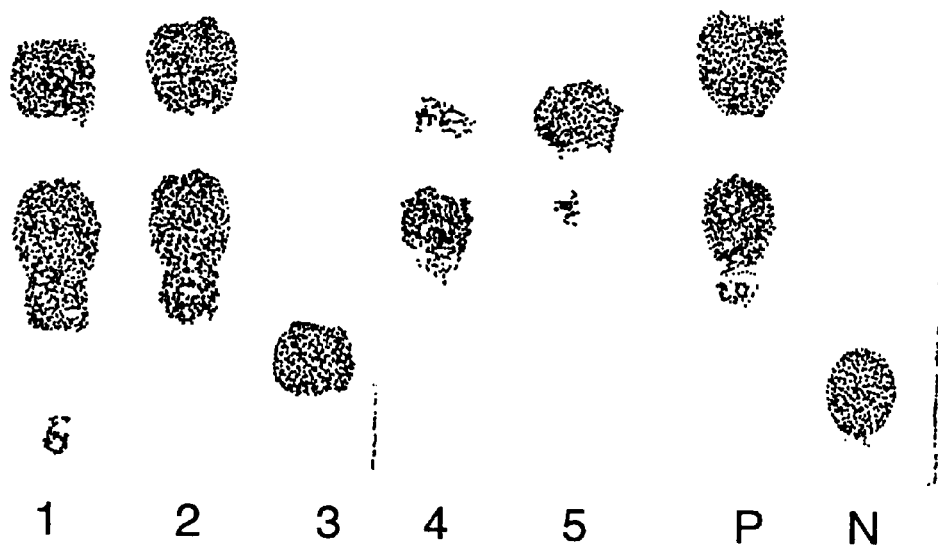
FIG. 1-B

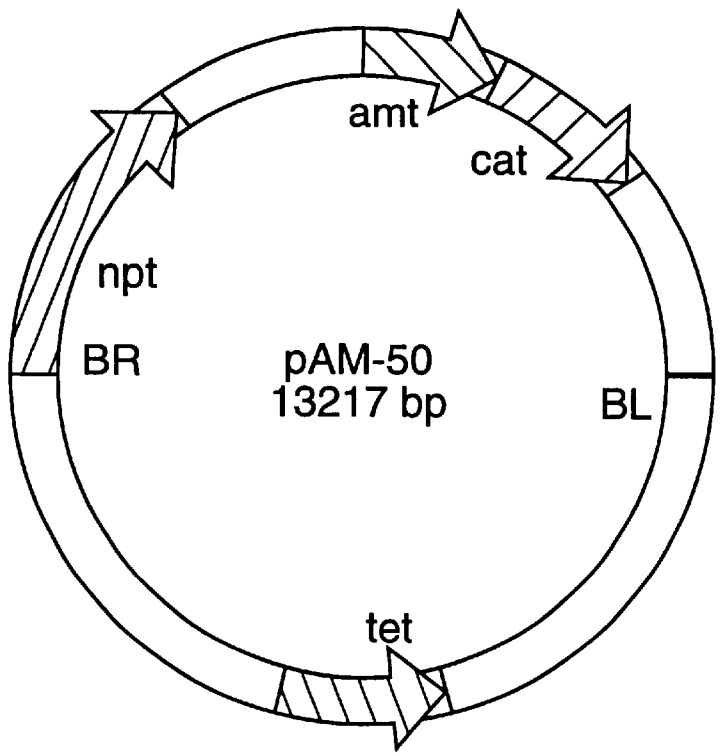
FIG. 2-A
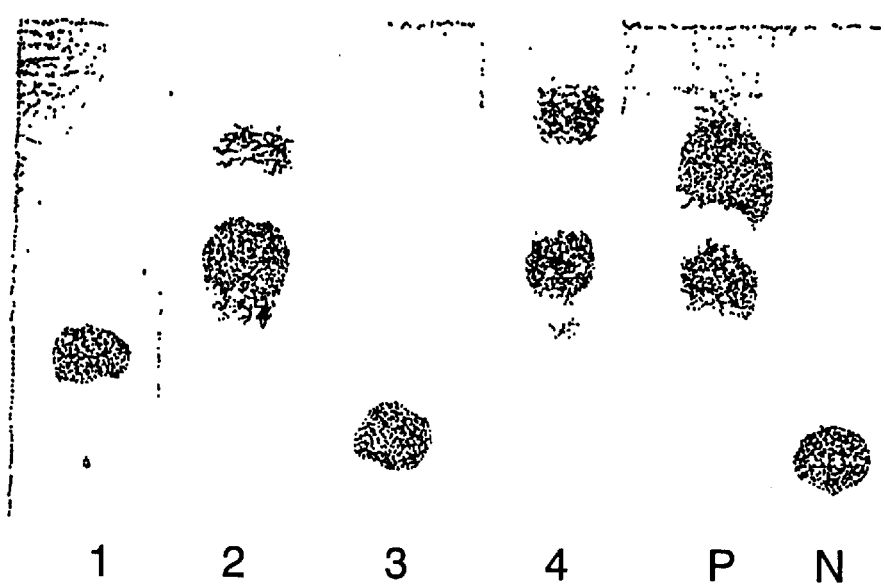
FIG. 2-B

CHLORAMPHENICOL ACETYLTRANSFERASE ACTIVITY

|  | TRANSIENT EXPRESSION | | STABLE TRANSFORMATION | |
|---|---|---|---|---|
|  | amt-cat | 35S-cat | amt-cat | 35S-cat |
| RICE |  |  |  |  |
| WHEAT |  |  |  |  |
| TOBACCO |  |  |  |  |
| *ARABIDOPSIS* |  |  |  |  |
| *AGROBACTERIUM* |  |  |  |  |
| *E. coli* |  |  |  |  |

FIG. 4

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 851 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
        (A) ORGANISM: Chlorella virus NC-1A (vii) IMMEDIATE SOURCE:
        (B) CLONE: AMT-1

(xi) SEQUENCE DESCRIPTION: SEQ ID NO:1:

```
ATCAGTAATG TGTTAATTGC GAACGCTTGT AATGGTGAAC GAATCCAATT CGGAAATGCA      60
GTCGACTACA ATTATTCTTT GACACCTTTG TTGACGACGC ATGCAAAGTT GAATATTGAC     120
AATCTCGTAT AAATTATTCG TTTATGCTGT TTCAAATCAT ATTGAAGTTC ACTGGTTTTA     180
GAGTGTCGAA AAGTATCATA TCAACGATTA TAGTATTTAA TGACAATACT CGCGACTGTC     240
ATAGTTTATT TTTCAACAAT GGAGTCTCGT CATCATATCA ATTTGACGAA TGTTGTTCGT     300
ATACAAAATA TAACAGATGA TTTTATTTGC GAATACGAAG ATTCTTCTTA TGGAGAAGAA     360
CCAGTTAATA ACAAATCGGA AGAAGTTCAT ACAGCGTTCA AATTATATGA CATAGATGAC     420
GAAACATTGT ACAATTATTA CAACGGAGTG GTCGTACATA CTACAAATGG ATTGCCAATA     480
GTATTCGCAA TGGATACACA CCGAGGTTGT TGCGAGAAAT TTTGTATCAC GGTACAATTA     540
CCAGGGGGCC TTACGCGATA TGATTTTATT GGCGCCACGA TTACGAAGGT AAGATTTGGT     600
AAAGAAAAAC GCAAATGCGA TATTAATTTT TCGGAATTAA TTATAGAAAC TTCGGTAGGA     660
AATATCGTTT TACTGGCAGA AAACATTCAT AATGGATATT ACTCTCATGA TGTATTCGCT     720
TGTTTTGAAG GTAAAGTTGA AACTTTTCGT TTGTAAATAC AAAAAATGTA TATGAGTATT     780
TGTTGTCGGA ATGTCATATC AACAATGTTG TGTATATATG TGTAAACTAA AATACACTAT     840
ATATTATTTA A                                                          851
```

(2) INFORMATION FOR SEQ ID NO:2:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Chlorella virus XZ-6E (vii) IMMEDIATE SOURCE:
        (B) CLONE: AMT-2

(xi) SEQUENCE DESCRIPTION: SEQ ID NO:2:

```
GAATTCTACT TATATACCAT ATCATTTTCC ATAACAAATT GAAAGTCGAA TGATTTACCA      60
CGTCCTCCGA TTTGTTCTAC GCTCTTCAAT TTTGTAATAT CAATGACATT TGAAATACTT     120
TCTAACAGTC TCTGTTGAAC ACTTGTATTT TCGTTAATAT CACGATTATT TAGTGTATCA     180
ACTATAATTT TTCTCGCTGC TTATTGTTAA TATCGTTGTC TCCGCGAATA CCTGTTACGA     240
AAATATCATC AGGATTATCC CGTTCCTTTT CAGCAAGTTT TTCCGCCTTT ACTCGTTCCT     300
TTTCAGCAAG TTTTTCCGCC TTTACTCGTT CCTTTTCAGC AAGTTTTTCC GCCTTTACTC     360
GTTCCTTTTC GATTTGCTA ACCTTTTTCA TTTTCATAAG ATTGATTATG TTTATAATAT     420
TCAGCATATT TATGTTCTGT TCACATATTA ATATATATAA ATAAAATGAC ACAAAAATGA     480
CACAAAAATG ACACAAAAAT GACACAAAAA TGACATAGAA TTTACACTTG TACACTAGAC     540
ACGTGTACAC AATATCATAT CAACATACGA AACAACTTAA ATTAAAAAAA ATGATTGATT     600
```

```
TTATAAATT                                                             609

(2) INFORMATION FOR SEQ ID NO:3:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Chlorella virus IL-3A (vii) IMMEDIATE SOURCE:
          (B) CLONE: CMT-1

(xi) SEQUENCE DESCRIPTION: SEQ ID NO:3:

TGTGATGAAC TTGAGTTTTA CAAAAATATT TCTGGTGGAA CTATATATTA TAGTCCATCA        60

GATAAGAATG TCGGATTTGT TATCATTCCC AAGGGTACAG AAGTCCATAT GAAATATGTT       120

AATCTTGATC AAGAATGATT GTCATTGTAT ATTTAAACCA TTTATACAAT AAGCGTTGAT       180

ATAAGTTTGT ATATACGTCA TTTCGTTATA TCAACAAATG TTATCATATT ATACGTAAAA       240

CTGGCTTAAA AAAAAACGAG TGTAACTATA                                       270

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
          (B) CLONE: Multirestriction site oligonucleotide (xi) SEQUENCE DESCRIPTION: SEQ ID NO:4:

GGTACCTCGA GGCCT                                                        15
```

PROMOTERS FROM CHLORELLA VIRUS GENES PROVIDING FOR EXPRESSION OF GENES IN PROKARYOTIC AND EUKARYOTIC HOSTS

This application is a divisional of application Ser. No. 08/268,072 filed Jun. 27, 1994, now U.S. Pat. No. 5,563,328, which is a continuation of application Ser. No. 07/932,334 filed Aug. 19, 1992, now abandoned.

BACKGROUND OF THE INVENTION

Genetic engineering has provided a method to isolate, selectively amplify, and express genes encoding desirable traits. These genes are often obtained from one organism and transformed into another organism so that expression of the gene can be manipulated and maximized. The transfer of genes from one organism to another can be used to produce large quantities of the gene product as well as to provide the transformed organism with improved characteristics or traits. Heterologous genes encoding desirable traits can be introduced into a wide variety of prokaryotic and eukaryotic hosts. For example, advantageous genes encoding herbicide resistance from bacteria can be incorporated into a plant's genome. The bacterial gene can then be expressed in the plant cell to confer on the plant cell resistance to the herbicide.

In order for the newly inserted gene to be expressed in a eukaryotic or prokaryotic host cell, proper regulatory sequences must be present and in the proper location with respect to the coding sequence. These regulatory sequences include a promoter region and a 3' nontranslated regulatory region. The promoter is a region of DNA sequences located upstream from the coding sequence of the gene. The function of a promoter sequence is to allow access and position of the transcription enzyme RNA polymerase in the vicinity of the transcription initiation site. The promoter DNA sequence can contain regulatory sequences that influence the rate and timing of the transcription of the gene. For example, insertion of a 21 base pair sequence into the 35S cauliflower mosaic virus (CaMV) promoter results in a tissue-specific expression in roots (Lam et al., PNAS, 86:7890 (1989).) Other sequences, like the TATA box and the CCAAT box in eukaryotic promoters, are known to influence the rate and level of gene transcription.

Certain promoters are known to be strong promoters. These promoters direct transcription at higher levels than other types of promoters and are capable of directing expression in other types of cells. One of the promoters that is a strong promoter in some types of plant cells is the 35S cauliflower mosaic virus (CaMV) promoter. However, the 35S CaMV promoter expression in plants can be variable and is especially so in monocotyledonous plants. Thus, strong promoters in one system often are not capable of providing for gene expression in a wide variety of both prokaryotic and eukaryotic host cells.

Chlorella viruses are a large group of recently identified viruses that infect certain eukaryotic green algae Chlorella. Chlorella viruses can be produced in large quantities and can be assayed by plaque formation. Chlorella viruses are large (150 to 190 nm) polyhedral plaque forming viruses containing greater than 300 kilobases of linear double-stranded DNA. The viruses are placed into 16 classes on the basis of plaque size antibody reactivity and the nature and abundance of methylated bases in their genomic DNA.

The Chlorella viruses have several unique features. The viruses have enough DNA sequence to encode 200 to 300 proteins. It is known that each virus contains and encodes 50 structural genes. The viruses also encode several DNA methyltransferase genes, DNA restriction endonuclease genes, and DNA polymerase genes. The DNA methyltransferase genes and the restriction endonuclease genes have been studied as a unique DNA restriction-modification system. Because the Chlorella viruses can be grown to large quantities and have several unique features, they are good candidates for the isolation of factors important in gene regulation.

Thus, there is a need for identifying and isolating strong promoters that are capable of expressing heterologous genes in a wide variety of cell types. There is also a need to identify and isolate strong promoters that can function in monocotyledonous plants, like wheat or rice. There is also a need to identify, isolate and characterize the promoters of the Chlorella virus genes including the DNA methyltransferase genes.

SUMMARY OF THE INVENTION

The invention is directed to novel promoters or mutants thereof from Chlorella virus DNA methyltransferase genes. These novel promoters are operably linked to a first DNA sequence encoding a gene that is different from the Chlorella virus gene to form an expression cassette. an expression cassette typically includes, a 3' nontranslated regulatory DNA sequence functional in eukaryotic cells and operably linked to the first DNA sequence. The preferred Chlorella virus DNA methyltransferase promoters in the expression cassette provide for a high level of constitutive gene expression in prokaryotic and eukaryotic cell hosts.

An expression cassette of the invention can further comprise a second DNA sequence encoding a different gene from the first DNA sequence. The second DNA sequence is linked to the first DNA sequence and under the control of the Chlorella virus promoter. The second DNA sequence preferably encodes a reporter gene or a selectable marker gene.

An expression cassette of the invention is introduced into prokaryotic and eukaryotic cells, preferably in a plasmid vector. Plasmid vectors including an expression cassette of the invention are used to stably transform prokaryotic cells. The preferred transformed prokaryotic species include *E. coli*, phytopathogenic members of the genera Pseudomonas and Erwinia, plant associated members of the genus Xanthomonas, with members of the genus Agrobacterium. Stably transformed prokaryotic cells are selected and are capable of transmitting an expression cassette to progeny cells. The transformed progeny cells express the genes encoded by the first and/or second DNA sequence under the control of the Chlorella virus promoters.

Eukaryotic cells, preferably plant cells, can be transformed with an expression cassette, typically in a binary $T_i$ vector. Transformed plant cells can transiently express the genes from the first and/or second DNA sequence. Transformed plant cells exhibiting transient gene expression, preferably monocotyledonous plant cells, can be converted to stably transformed or transgenic plants. Transformed plant cells are incubated in the presence of callus induction medium and a selective agent. Transformed calli can then be used to generate the transformed or transgenic plants. The transgenic plants can be grown and selfed or crossed to produce transgenic progeny plants and seeds. The preferred transqenic plant of the invention is a monocotyledonous plant having a Chlorella virus promoter that provides for a high level of constitutive gene expression.

The invention also provides a method for screening other Chlorella virus genes for promoters that can function to express a heterologous gene in prokaryotic and/or eukaryotic hosts. Chlorella virus genes with their flanking DNA sequences are isolated, sequenced, and the coding region of the gene identified. Once the Chlorella virus gene and its 5' flanking sequence been identified, a method of the invention involves isolating a DNA fragment including about 50 to 2000 nucleotide base pairs of the DNA sequence upstream from the coding sequence. An expression cassette is formed by combining the DNA fragment with a reporter gene, like chloramphenicol acetyltransferase. An expression cassette is used to transform prokaryotic and/or eukaryotic hosts and expression of the reporter gene is detected. Promoter sequences providing for a high level of gene expression in eukaryotic and/or prokaryotic hosts can be identified.

BRIEF DESCRIPTION OF THE DRAWINGS

FIG. 1 shows expression of AMT-CAT fusion construct (ColEI) in various phytopathogenic bacteria. 2 μg of plasmid DNA was used to transform bacterial cells by the standard calcium coprecipitation method. Chloramphenicol acetyltransferase (CAT) assay was performed using 10 μg of total protein at 37° C. for 60 minutes to determine the adenyl methyltransferase (AMT) promoter activity. The Lanes are identified as follows: 1. *E. coli*, MC1000; 2. *E. coli*, JM83; 3. *Bacillus pumulis*; 4. *Erwinia amylovora*; 5. *Erwinia carotovora*; P=positive CAT control; and N=negative CAT control.

FIG. 2 shows expression of AMT-CAT fusion construct (RK-2) in various phytopathogenic bacteria. 2 μg of plasmid DNA was used to transform bacterial cells by electroporation using 6250 V/cm, 25 uf capacitor, and Pulse Controller at 400 ohms. The Lanes are identified as follows: *Clavibacter michiganense* ssp. Nebraskense (Lane 1); *Pseudomonas syringae* pv. *syringae* (Lane 2); *Xanthomonas campestris* pv. *asclepiadis* (Lane 3); and *Agrobacterium tumefaciens* (Lane 4). The positive CAT control is shown in Lane 5 and the negative control in Lane 6.

FIG. 3 shows analysis of promoter activity of AMT-5' deletion mutants in *E. coli* MC1000. *E. coli* competent cells were chemically transformed by calcium co-precipitation and analyzed for CAT activity. The deletion end points are shown at the left.

FIG. 4 shows expression of AMT-CAT fusion constructs in various systems. 35S-CAT expression was used to compare the AMT promoter activity. AMT-CAT and 35S-CAT constructs were used to compare the AMT promoter activity. AMT-CAT and 35S-CAT constructs were used to electroporate wheat, rice and tobacco cells and to transform competent *E. coli* and Agrobacterium cells. Same constructs were used in binary vectors for Agrobacterium medicated stable transformation of tobacco and Arabidopsis calli. CAT activity was determined by using 2 μg total protein incubated for 20 minutes at 37° C.

DETAILED DESCRIPTION OF THE INVENTION

This invention is directed to novel promoters from Chlorella virus genes that provide for a high level of gene expression in prokaryotic and/or eukaryotic cells. A promoter associated with a Chlorella virus gene is isolated and operably linked to a DNA sequence encoding a gene different from that of the Chlorella virus gene in an expression cassette. An expression cassette can be further comprised of a 3' nontranslated regulatory DNA sequence functional in eukaryotic cells and/or a second DNA sequence encoding a selectable marker gene. An expression cassette can also be further comprised of plasmid DNA or a binary $T_i$ vector DNA. The vector so formed can be used to deliver an expression cassette to the prokaryotic or eukaryotic cells. Transformed bacterial cells, preferably Agrobacterium, express high levels of the gene under the control of the Chlorella virus gene promoter. Transformed plant cells also express the gene or genes controlled by the Chlorella virus promoters at high levels and can be used to generate transgenic plants.

1. Formation of an Expression Cassette

A. Promoters

The promoters of the invention are obtained or modified from Chlorella virus genes. Chlorella viruses are large (150 to 190 nm) polyhedral plaque-forming viruses containing >300 kb of linear double-stranded DNA. At least 37 strains of the virus that infect eukaryotic Chlorella-like green algae have been isolated and partially characterized. The viruses are placed into 16 classes on the bases of plaque size, antibody reactivity, and the nature and abundance of methylated bases in their genomic DNA. Each of the viral DNAs contains 5-methylcytosine at a percentage of cytosine ranging from 0.1% to 47.5%. In addition, 25 of the 37 viral DNA also contain $N^6$ methyladenine as a percentage of adenine ranging from 1.45% to 37%. The finding of sequence specific methylation led to the discovery that these viruses have genes encoding DNA methyltransferases and site-specific endonucleases. In addition, these viruses contain at least 50 structural genes.

Some of the Chlorella virus genes, including the 5' flanking regions, have been isolated and sequenced. Four of the viral-encoded DNA methyltransferase genes have been isolated and sequenced, as reported by Shields et al., *Virology*, 176:16 (1990); Stefan et al., *Nucleic Acids Res.*, 19:307 (1991); Narva et al., *Nucleic Acids Res.*, 15:9807 (1987); and Zhang et al., *Nucleic Acid Res.* (submitted for publication). Two DNA polymerase genes including 5' flanking regions from Chlorella viruses PBCV-1 and NY-2A were isolated and sequenced, as described by Grabherr et al., *Virology*, 188:721 (1992).

Most genes have regions of DNA sequence that are known promoters and which regulate gene expression. Promoter regions are typically found in the flanking DNA sequence upstream from the coding sequence in both prokaryotic and eukaryotic cells. A promoter sequence provides for regulation of transcription of the downstream gene coding sequence and typically includes from about 50 to 2000 nucleotide base pairs. Eukaryotic promoters usually contain a consensus sequence known as the TATA box region, 20–30 base pairs (bp) upstream from the transcription initiation site. A second eukaryotic consensus sequence, the CCAAT box region, is also found at about 80 bp upstream from the transcription initiation site. Prokaryotic promoters typically a have a TATAAT consensus sequence 10 bp upstream from the start codon, and a TTGACA 35 bp upstream from the start codon. These consensus sequences, as well as other promoter regulatory sequences, can be present and function to regulate levels of gene expression. For example, a 21 bp element has been identified in the 35S cauliflower mosaic virus promoter as providing for root specific gene expression, as described by Lam et al., *PNAS*, 86:7890 (1989).

Promoter DNA sequences are found upstream and are associated with expression of a particular gene. The gene regulated by the promoter sequence can be referred to as the native or homologous gene. Some isolated promoter DNA sequences can provide for gene expression of a heterologous gene, that is a gene different from the native or homologous gene. Promoter sequences are also known to be strong or weak. A strong promoter provides for a high level of gene expression, whereas a weak promoter provides for a low level of gene expression. An isolated promoter sequence that is a strong promoter for heterologous genes has great utility and offers many advantages in the transfer of genes from one organism to another by recombinant DNA techniques.

Some of these advantages include providing a sufficient level of gene expression to allow for easy detection and selection of transformed cells expressing the heterologous gene. Another advantage is to replace the native or homologous promoter with a promoter sequence known to provide for a high level of gene expression. A third advantage is to allow for the transfer of genes for which a promoter has not been identified.

The promoters of the invention are promoters or mutants thereof of Chlorella virus genes. The promoters can provide for gene expression in prokaryotic and/or eukaryotic hosts. The promoters also provide for gene expression of heterologous genes. A heterologous gene is a gene which is different from the Chlorella virus gene from which the Chlorella virus promoter is obtained. The heterologous gene can be obtained from different organisms, like a bacteria, plant or mammal. The promoters of the invention preferably include from about 50 bp to 2000 bp more preferably 500 to 2000 bp of DNA sequence and can contain regulatory sequences. The promoters of the invention can also include from about 3 to about 150 nucleotides of the coding sequence of the Chlorella virus gene from which the promoter is obtained.

The preferred promoters of the invention are promoters that substantially correspond to promoters for Chlorella virus DNA methyltransferase genes. A promoter that substantially corresponds to the promoters for DNA methyltransferase genes shares about 85% to 100% DNA sequence homology with that promoter while retaining the capacity to provide for expression of a heterologous gene. These promoters can preferably function in both prokaryotic and eukaryotic cells. The preferred promoters also provide for a high level of constitutive expression of heterologous genes.

The promoter designated AMT-1 is found within about 850 bp upstream from the adenyl methyltransferase gene M.CviBIII from Chlorella virus NC-1A. The promoter designated AMT-2 is found within about 610 bp from the start codon for the adenyl methyltransferase gene M.CviRI from Chlorella virus XZ-6E. The promoter sequence designated CMT-1 is found within about 500 bp upstream from the start codon for the cytosine methyltransferase gene M.CviJI from Chlorella virus IL-3A. The adenyl methyltransferase promoters AMT-1 and AMT-2 lack the eukaryotic consensus sequences (TATA and CCAAT) and prokaryotic consensus sequences (CTATAAT and TTGACA).

The sequence of the AMT-1 promoter is shown in Table I (SEQ ID NO: 1). The sequence of the AMT-2 promoter is shown in Table II (SEQ ID NO: 2). The sequence of the CMT-1 promoter is shown in Table III (SEQ ID NO: 3).

TABLE I

SEQUENCE OF THE AMT-1 PROMOTER

ATCAGTAATG TGTTAATTGC GAACGCTTGT AATGGTGAAC

GAATCCAATT CGGAAATGCA GTCGACTACA ATTATTCTTT

GACACCTTTG TTGACGACGC ATGCAAAGTT GAATATTGAC

AATCTCGTAT AAATTATTCG TTTATGCTGT TTCAAATCAT

TABLE I-continued

SEQUENCE OF THE AMT-1 PROMOTER

ATTGAAGTTC ACTGGTTTTA GAGTGTCGAA AAGTATCATA

TCAACGATTA TAGTATTTAA TGACAATACT CGCGACTGTC

ATAGTTTATT TTTCAACAAT GGAGTCTCGT CATCATATCA

ATTTGACGAA TGTTGTTCGT ATACAAAATA TAACAGATGA

TTTTATTTGC GAATACGAAG ATTCTTCTTA TGGAGAAGAA

CCAGTTAATA ACAAATCGGA AGAAGTTCAT ACAGCGTTCA

AATTATATGA CATAGATGAC GAAACATTGT ACAATTATTA

CAACGGAGTG GTCGTACATA CTACAAATGG ATTGCCAATA

GTATTCGCAA TGGATACACA CCGAGGTTGT TGCGAGAAAT

TTTGTATCAC GGTACAATTA CCAGGGGCC TTACGCGATA

TGATTTTATT GGCGCCACGA TTACGAAGGT AAGATTTGGT

AAAGAAAAAC GCAAATGCGA TATTAATTTT TCGGAATTAA

TTATAGAAAC TTCGGTAGGA AATATCGTTT TACTGGCAGA

AAACATTCAT AATGGATATT ACTCTCATGA TGTATTCGCT

TGTTTTGAAG GTAAAGTTGA AACTTTTCGT TTGTAAATAC

AAAAAATGTA TATGAGTATT TGTTGTCGGA ATGTCATATC

AACAATGTTG TGTATATATG TGTAAACTAA AATACACTAT

ATATTATTTA A

TABLE II

SEQUENCE OF THE AMT-2 PROMOTER

GAATTCTACT TATATACCAT ATCATTTTCC ATAACAAATT

GAAAGTCGAA TGATTTACCA CGTCCTCCGA TTTGTTCTAC

GCTCTTCAAT TTTGTAATAT CAATGACATT TGAAATACTT

TCTAACAGTC TCTGTTGAAC ACTTGTATTT TCGTTAATAT

CACGATTATT TAGTGTATCA ACTATAATTT TTCTCGCTGC

TTATTGTTAA TATCGTTGTC TCCGCGAATA CCTGTTACGA

AAATATCATC AGGATTATCC CGTTCCTTTT CAGCAAGTTT

TTCCGCCTTT ACTCGTTCCT TTTCAGCAAG TTTTTCCGCC

TTTACTCGTT CCTTTTCAGC AAGTTTTTCC GCCTTTACTC

GTTCCTTTTC GATTTTGCTA ACCTTTTTCA TTTTCATAAG

ATTGATTATG TTTATAATAT TCAGCATATT TATGTTCTGT

TCACATATTA ATATATATAA ATAAAATGAC ACAAAAATGA

CACAAAAATG ACACAAAAAT GACACAAAAA TGACATAGAA

TTTACACTTG TACACTAGAC ACGTGTACAC AATATCATAT

CAACATACGA AACAACTTAA ATTAAAAAAA ATGATTGATT

TTATAAATT

TABLE III

SEQUENCE OF THE CMT-1 PROMOTER

```
TGTGATGAAC TTGAGTTTTA CAAAAATATT TCTGGTGGAA

CTATATATTA TAGTCCATCA GATAAGAATG TCGGATTTGT

TATCATTCCC AAGGGTACAG AAGTCCATAT GAAATATGTT

AATCTTGATC AAGAATGATT GTCATTGTAT ATTTAAACCA

TTTATACAAT AAGCGTTGAT ATAAGTTTGT ATATACGTCA

TTTCGTTATA TCAACAAATG TTATCATATT ATACGTAAAA

CTGGCTTAAA AAAAAACGAG TGTAACTATA
```

Mutants of the Chlorella virus promoters include those in which the DNA sequence has been changed including a deletion of nucleotides, insertion of nucleotides, and/or substitution of nucleotides. Mutants preferably contain a functional fragment of the native Chlorella virus promoter. Mutants of the promoters of the Chlorella virus genes can be generated by standard methodologies including terminal and internal deletion mutagenesis, as described by Mitra et al., *Molecular Gen. Genetics*, 215:294 (1989); insertional mutagenesis and site-specific mutagenesis, as described by Lam et al., *PNAS*, 86:7890 (1989). Deletion mutants can be generated, usually lacking at least one nucleotide from either the 5' or 3' terminal ends of the promoter sequence. Internal deletion mutants of the promoter can be lacking at least one nucleotide in the internal portion of the promoter sequence. The insertional mutants can be generated by adding DNA sequence either synthesized by automated methods or subcloned from another genome and inserted into an intact promoter or a 5' or 3' deletion mutant. A mutant promoter sequence can also be generated by site-specific mutagenesis by insertion of a synthesized oligonucleotide sequence having site-specific mutations. The synthetic oligonucleotide sequence can be inserted into the promoter at a specific restriction endonuclease site. Mutant promoter sequences can be tested for the ability to provide for expression of a heterologous gene by the method of the invention.

Deletion mutants removing up to about 300 bp from the 5' terminus of the AMT-1 promoter are the preferred mutants for providing an AMT promoter that selectively functions in bacterial cells and does not function in tobacco cells. Other deletion mutants generated from the 3' end or internally, as well as insertion mutants, can provide for selective expression in plant cells and tissue specific expression in plants.

Promoters from Chlorella virus genes are identified usually in the AT-rich 5' flanking regions of the coding sequence of Chlorella virus genes, preferably DNA methyltransferase genes. Once identified as a putative promoter sequence, the promoter sequence is subcloned by digesting the cloned Chlorella gene sequence with restriction endonucleases to isolate the promoter region and optionally about 3 to 150 nucleotides of the Chlorella virus gene coding sequence. Mutants of the promoter sequence can be generated as described previously. The digested promoter or mutant promoter sequence is operably linked to a promoterless heterologous gene, such as the chloramphenicol acetyltransferase gene in a plasmid, and ligated with $T_4$ DNA ligase. The resulting plasmids are introduced into prokaryotic and/or eukaryotic cells. Transformed bacteria or plant cells can be selected, preferably for antibiotic resistance. The selected bacterial or plant cells are then assayed for expression of the heterologous gene under the control of the Chlorella virus promoter.

Other promoters are present in the Chlorella virus genomes and can be identified and tested for the ability to provide for expression of heterologous genes in both eukaryotic and prokaryotic cells in a method provided for in the invention. For example, DNA polymerase genes from Chlorella virus PBCV-1 and NY-2A have been isolated and sequenced, as described by Grabherr et al., cited supra. The cloned gene sequence includes about 160 to 170 nucleotides upstream that are AT rich and could function as a promoter. This 5' region of the Chlorella virus DNA polymerase genes can be isolated by restriction endonuclease digestion and subcloned into a ColEI plasmid or binary Ti vector upstream from a promoterless reporter gene, such as chloramphenicol acetyltransferase gene. Subcloning this putative promoter region immediately upstream from a promoterless reporter gene such as chloramphenicol acetyltransferase genes, provides a method for testing whether the DNA sequence having potential promoter activity can function to express a heterologous gene in a prokaryotic and/or eukaryotic cell. The ColEI plasmids or binary $T_i$ vectors can be introduced into prokaryotic or eukaryotic cells and transformed cells can be assayed for expression of the reporter gene, such as chloramphenicol acetyltransferase gene. Thus, other putative Chlorella virus gene promoters can be identified, isolated and tested for the ability to provide for gene expression in both prokaryotic and/or eukaryotic cells.

B. DNA Sequence Encoding a Heterologous Gene Different from the Chlorella Virus Gene An expression cassette is formed by combining one or more DNA sequences encoding desired genes with transcriptional and translational regulatory DNA sequences that provide for gene expression in a particular cell type. The DNA sequences are combined so that the transcriptional and translational control regions are operably linked to the DNA coding sequence and can function to provide for gene expression. When one or more DNA sequences coding for genes are combined with a different promoter sequence than the native sequence, the resulting product can be called a "DNA construct" or a "fused gene".

An expression cassette of the invention is formed by combining a promoter or mutant thereof from a Chlorella virus gene with one or more DNA sequences that encode a gene different from the Chlorella virus gene. The DNA sequence preferably encodes a gene that provides a desired characteristic in a prokaryotic or eukaryotic host. The gene can be another Chlorella virus gene, from a prokaryotic or a eukaryotic organism. The gene can also serve as a selectable marker or reporter gene. The desired gene will be selected depending upon whether expression is desired in prokaryotic cells, eukaryotic cells, or both, and depending on the desired trait.

Specific examples of the types of genes that can form an expression cassette of the invention include plant cell genes of economic importance, like growth promoter genes, disease resistance genes, frost and drought tolerance genes, herbicide and insecticide resistance genes, and the like. Desired bacterial genes include genes of economic importance for phyllosphere or rhizosphere bacteria associated with plants such as genes encoding oxalic acid degradation, genes encoding chitinase, genes encoding lignin degradation, and genes encoding biosynthesis of phenazine effective to control wheat root disease. In phytopathogenic bacteria, it is desirable to include genes that encode antisense messages for toxin genes that are associated with plant disease such as tagetoxin. Other genes encoding antisense messages can be selected from those described in *Plant Pathogenic Bacteria*, Klement et al. editors, Proceedings of the 7th International conference on Plant pathogenic Bacteria, Part A/Part B (1990). Desired eukaryotic genes include genes for peptide hormones, growth factors, cytokines, and the like. The DNA sequence can also encode a selectable marker gene or a reporter gene that provides for selection of the transformed prokaryotic or eukaryotic cells.

The preferred first DNA sequence of the expression cassette encodes resistance to a herbicide such as the 5-enol-pyruvyl-phosphoshikimate gene that encodes resistance to the herbicide glyphosate. The preferred first DNA sequence for use in transformation of phytopathogenic bacteria encodes an antisense expression of pathogenic determinate, such as a toxin.

An expression cassette of the invention can also include a second DNA sequence linked to the first DNA sequence and different from the first DNA sequence. The second DNA sequence preferably encodes a selectable marker gene or a reporter gene.

Specific examples of selectable marker genes are neomycin phosphotransferase gene, apramycin resistance gene, hygromycin β-phosphotransferase gene, dihydrofolate reductase gene, guanine phosphoribosyl transferase gene, and the thymidine kinase gene. The second DNA sequence can also encode a reporter gene such as chloramphenicol acetyltransferase, β-galactosidase, β-glucuronidase, and human growth hormone.

Once the desired gene is selected, its DNA sequence can be isolated from the source organism by standard methodologies, as provided in Sambrook et al., *Molecular Cloning: A Laboratory Manual,* 2nd Ed., Cold Spring Harbor Laboratory, Cold Spring, N.Y. (1989). Generally, once a desired gene is selected, a DNA library is prepared from the source organism. Clones of DNA having the desired gene are detected by a variety of methods, including hybridization to oligonucleotide probes or detection of expression of the gene product. DNA clones containing the gene can be subcloned and sequenced.

Once sequenced, the portion of the DNA sequence encoding the coding sequence for the gene and lacking a functional native promoter can be combined with Chlorella virus promoter in a ColEI plasmid or binary $T_i$ vector. Briefly, the DNA sequence encoding the gene and the ColEI plasmid or the binary $T_i$ vector are digested with one or more restriction endonucleases and then ligated together with $T_4$ DNA ligase. Resulting plasmids incorporating the desired gene lacking all or part of the native promoter are selected and amplified, usually in a bacterial host. The plasmid carrying the desired gene can then have a Chlorella virus promoter sequence inserted upstream so that the promoter is operably linked to DNA coding sequence, typically at a different restriction endonuclease site. Alternatively, the promoter sequence and the DNA sequence encoding the gene can be ligated together first and then inserted into a plasmid for selection and amplification.

C. 3' Nontranslated Regulatory Region

Optionally, when necessary for efficient gene expression, the expression cassette can include a 3'; nontranslated regulatory DNA sequence. The 3' nontranslated regulatory DNA sequence preferably includes from about 3 to 1000 nucleotide base pairs (bp) and contains transcription and/or translation termination sequences. The 3' nontranslated regions can be obtained from the flanking regions of genes from bacterial, plant, or other eukaryotic cells. For transcription efficiency and termination of a first DNA sequence encoding a prokaryotic gene, the 3' flanking sequences can include a transcription termination sequence. For transcription efficiency and termination of a first DNA sequence encoding a eukaryotic gene, the 3' flanking sequence has a polyadenylation sequence that functions to add a polyA tail to the messenger RNA. The 3' nontranslated regions are operably linked to the first and/or second DNA sequence to provide for gene expression in prokaryotic and eukaryotic cells by standard methodologies, as described in Sambrook et al., cited supra.

Specific examples of the 3' nontranslated regulatory DNA sequences functional in eukaryotic cells include about 500 bp of 3' flanking DNA sequence of the pea ribulose biphosphate carboxylase small subunit E9 gene, 3' flanking DNA sequence of the octopine synthase gene, the 3' flanking DNA sequence of the nopaline synthase gene, and SV40 polyadenylation and transcription termination sequences. Especially preferred are the 3' nontranslated regulatory DNA sequences that function in plant cells such as the 3' flanking DNA sequence from the octopine synthase or nopaline synthase genes.

The 3' nontranslated DNA regulatory regions are often already present in plasmid vectors used for selection amplification and transformation of prokaryotic and eukaryotic cells. Typically, the desired first and/or second DNA sequence encoding the desired genes are inserted immediately upstream from 3' nontranslated DNA regulatory sequence so that the DNA sequences are operably linked together. Alternatively, the 3' nontranslated DNA regulatory regions known to be functional in prokaryotic or eukaryotic cells can be isolated from a cloned gene sequence by restriction endonuclease digestion. Once isolated, the 3' flanking region DNA sequence can be inserted downstream from the first or second DNA sequence by standard subcloning methods, as described by Sambrook et al., cited supra.

2. Formation of a Vector Containing the Expression Cassette

Vectors include additional DNA sequences that provide for easy selection, amplification, and transformation of the expression cassette in prokaryotic and eukaryotic cells. The additional DNA sequences include origins of replication to provide for autonomous replication of the vector, selectable marker genes preferably encoding antibiotic resistance, unique multiple cloning sites providing for multiple sites to insert the expression cassette, and sequences that enhance transformation of prokaryotic and eukaryotic cells. The preferred vectors of the invention are plasmid vectors. The especially preferred vectors are the ColEI plasmid vector or the binary $T_i$ vector pGA582.

ColEI plasmid vectors, such as pUC18 and pUC19, have been previously characterized by Yanisch-Perron et al., *Gene,* 33:103 (1985) and are available from Stratagene or New England BioLabs. A ColEI plasmid vector is a 2.7 kbp plasmid and contains an origin of replication that provides for autonomous replication in both prokaryotic and eukaryotic cells. A ColEI plasmid also contains selectable marker genes encoding antibiotic resistance. A ColEI plasmid contains multiple cloning sites providing for insertion of an expression cassette of the invention. A ColEI plasmid carrying an expression cassette of the invention can be used to transform both prokaryotic and eukaryotic cells.

The binary $T_i$ vector pGA582 has been previously characterized by An, *Methods in Enzymology,* 153:292 (1987) and is available from both Dr. An and Dr. Mitra. The binary $T_i$ vector can replicate in prokaryotic bacteria, such as *E. coli,* and in Agrobacterium. The Agrobacterium plasmid vectors can be used to transfer the expression cassette to plant cells. The binary $T_i$ vectors preferably include the nopaline T-DNA right and left borders to provide for efficient plant cell transformation, a selectable marker gene, unique multiple cloning sites in the T-border regions, the ColEI replication of origin, and a wide host range replicon. The binary $T_i$ vectors carrying an expression cassette of the invention can be used to transform both prokaryotic and eukaryotic cells, but is preferably used to transform plant cells.

A vector of the invention can also include a vector that can transform algal cells, including species of Chlorella. For example, Jarvis et al., Current Genetics, 19:317 (1991) have described the use of plasmid pDO432 derived from the E. coli pUC19 plasmid. This plasmid can contain a reporter gene, the nopaline synthase polyadenylation site, and the portion of the pUC19 cloning vector (Yanisch-Perron et al., Gene, 33:103 (1985)) including the gene for ampicillin resistance and an origin of replication. A Chlorella virus promoter fused to a gene encoded by the first DNA sequence can be introduced upstream from the reporter gene in a plasmid such as pDO432. The plasmid vector can be used to transform. Chlorella species and other species of green algae.

A vector of the invention can also be a virus vector. Virus vectors can provide for efficient cloning and gene expression in both prokaryotic and eukaryotic cells. Specific examples of virus vectors of the invention include the M13 phage system, the vaccinia virus expression system, and the baculovirus expression system.

An expression cassette of the invention can be inserted into or formed within a plasmid or virus vector by standard methods. Briefly, the Chlorella virus promoter or a mutant thereof can be combined with the first DNA sequence encoding a gene having the desired trait to form a fused DNA construct. Optionally, a 3' nontranslated DNA regulatory region can also be operably linked to the first DNA sequence. The fused DNA construct can then be inserted into one of the multiple cloning sites of the plasmid vectors by digestion with an appropriate restriction endonuclease and ligation with a ligase enzyme.

Alternatively, each of the DNA sequences in an expression cassette can be subcloned into the vector separately. For example, in a binary $T_i$ vector having multiple cloning sites, a Chlorella virus promoter sequence can be inserted at a unique restriction endonuclease site by digestion with that restriction endonuclease followed by ligation. A first DNA sequence can then be inserted at a different restriction endonuclease site immediately downstream from the Chlorella virus promoter sequence. Optionally, and if not already present in the vector, a second DNA sequence encoding a selectable marker gene can be inserted at another restriction endonuclease site downstream from the first DNA sequence. In addition, optionally, if not already present, a 3' nontranslated regulatory DNA sequence can be inserted immediately downstream from the first or second DNA sequence so that the 3' nontranslated DNA sequence is operably linked to the first or second DNA sequence.

The preferred plasmid of the invention has the characteristics of the ColEI plasmid carrying an expression cassette including the AMT-1 promoter fused to a promoterless chloramphenicol acetyltransferase gene. The AMT promoter provides for a high level of constitutive gene expression in both prokaryotic and eukaryotic cells. This ColEI plasmid has been designated pAM-15 and has been deposited with the American Type Culture Collection, Rockville, Md. in E. coli Jm 83 amp$^R$ bacteria on Sep. 8, 1992, and given Accession No. 69069.

The especially preferred plasmid has the characteristics of a binary $T_i$ vector carrying the AMT promoter fused to a promoterless chloramphenicol acetyltransferase gene and also encoding a neomycin phosphotransferase gene. The AMT promoter provides a high level of constitutive gene expression in plant cells.

3. Transformation of Prokaryotic and Eukaryotic Cells With An Expression Cassette Having a Chlorella Virus Promoter An expression cassette is introduced into prokaryotic and/or eukaryotic host cells to provide those cells with the capacity to express the desired gene encoded by the first and/or second DNA sequence under control of the Chlorella virus promoter. Cells containing an expression cassette and expressing the gene or genes encoded by the first and/or second DNA sequence are referred to as "transformed cells". Gene expression in transformed cells can be detected by a variety of methods including oligonucleotide probe hybridization to messenger RNA (mRNA), assay for the functional activity of the gene product, or detection of the gene product by its physical characteristics. Gene expression in transformed cells can be transient or stable. Transient gene expression is measured up to about 72 hours after transformed cells carrying the expression cassette are selected and identified. While not in any way meant to limit the invention, transient expression indicates that the expression cassette is transferred into the cells, the first and/or second DNA sequence is being transcribed and translated, and that the gene products are reasonably stable in the cell. Stable transformation is exhibited when the cells have replicated and the expression cassette can be shown to have been heritably transmitted and expressed in progeny cells or organisms. When genes are expressed continuously, gene expression is called constitutive. When gene expression is turned on and off, gene expression is called inducible.

An expression cassette of the invention is introduced into prokaryotic and eukaryotic cells. The transformed cells can be selected and/or assayed for stable and/or transient gene expression.

An expression cassette of the invention is introduced into prokaryotic host cells. The expression cassette is preferably present in a plasmid vector such as ColEI plasmid vector or the binary $T_i$ vector. The preferred prokaryotic hosts are E. coli, phytopathogenic bacteria including members of the genera, Pseudomonas and Erwinia, plant associated non-pathogenic bacteria of the genus Xanthomonas, and members of the genus Agrobacterium. Especially preferred bacterial hosts are members of the genus Agrobacterium that can then be used to transform plant cells.

An expression cassette can be introduced into bacterial hosts by standard methods, preferably by the calcium co-precipitation method. Transformed cells carrying an expression cassette in a plasmid can be first selected for antibiotic resistance encoded by a selectable marker gene present in the plasmid vector. Colonies resistant to the antibiotic and/or transformed cells are analyzed for expression of the gene encoded by the first and/or second DNA sequence by either mRNA hybridization, assay of gene product activity, or detection of the presence of the gene product. Typically, prokaryotic host cells are stably transformed with an expression cassette and can heritably transmit the expression to the progeny cells.

In a preferred version, phytopathogenic species of the genus Pseudomonas and Erwinia are transformed with ColEI plasmid vector carrying the AMT-1 promoter fused to a promoterless gene such as the chloramphenicol acetyltransferase gene. The transformed bacterial cells can be selected for antibiotic resistance and then assayed for gene expression of the chloramphenicol acetyltransferase gene. The chloramphenicol acetyltransferase gene can serve as the first or second DNA sequence. When the chloramphenicol acetyltransferase (CAT) gene serves as the second DNA sequence, CAT activity can be monitored as a reporter gene for the selection of transformed cells carrying the Chlorella virus promoters fused to a first DNA sequence encoding the desired gene. The preferred AMT promoter provides for a high level of constitutive gene expression in both *E. coli* and phytopathogenic bacteria.

In the especially preferred version, a binary $T_i$ vector carrying the AMT-1 promoter fused to CAT DNA constructs is introduced into Agrobacterium species from *E. coli*. The binary $T_i$ vector is transferred into an Agrobacterium species having a helper $T_i$ plasmid. The host Agrobacterium strain and helper $T_i$ plasmid can be selected depending on the plant species to be transformed. The binary vectors can be transferred to Agrobacterium species by a triparental mating method or direct DNA transfer method as described by An, *Methods in Enzymology*, 153:292 (1987).

Plasmid vectors carrying an expression cassette comprising a mutant of the Chlorella virus promoter fused to a first DNA sequence can also be introduced into prokaryotic or eukaryotic host cells. Transformed cells can be initially selected, preferably by resistance to an antibiotic. Antibiotic resistant cells or transformed cells are examined for expression of the gene encoded by the first and/or second DNA sequence. The mutant Chlorella virus promoter sequences can provide for selective expression in prokaryotic or eukaryotic cells and can also provide for tissue-specific expression. The preferred mutants are deletion mutants of the Chlorella virus AMT-1 promoters.

An expression cassette of the invention can be introduced into eukaryotic cells, preferably plant cells. An expression cassette preferably in a ColEI or binary $T_i$ plasmid vector can be introduced into eukaryotic cells by direct DNA transfer techniques such as protoplasting, electroporation, biolistic transformation, and Agrobacterium-mediated transformation. The preferred plant cells to be transformed include corn, rice, wheat, tobacco, and Arabidopsis cells. The especially preferred cells are from monocotyledonous plants such as rice, corn or wheat.

Other types of eukaryotic cells can also be transformed by vectors including an expression cassette of the invention. Eukaryotic cells such as yeast can be transformed using the calcium phosphate coprecipitation method. A Chlorella virus promoter of the invention can also be inserted into other vectors useful to transform eukaryotic cells. For example, a Chlorella virus promoter can be inserted into viral expression systems such as vaccinia virus. Once inserted into these expression systems, they can be combined with a DNA sequence encoding the desired gene to provide for gene expression in eukaryotic cells.

In a preferred version, a binary $T_i$ vector or a ColEI plasmid carrying the AMT-1 promoter fused to a reporter gene, such as a promoterless chloramphenicol acetyltransferase gene, is introduced into wheat, corn, rice and tobacco cells by electroporation. Transformed plant cells are examined for transient expression of reporter gene acetyltransferase by detection of the enzymatic activity within about 72 hours of transformation. The chloramphenicol acetyltransferase gene can be encoded by the first or second DNA sequence. When encoded by the second DNA sequence, the chloramphenicol acetyltransferase gene serves as a reporter gene that provides for identification of plant cells transformed with the first DNA sequence encoding the desired trait and expressed under the control of the Chlorella virus promoter. The preferred AMT promoter provides for a high level of constitutive gene expression in plant cells.

Transformed plant cells exhibiting transient gene expression under control of a Chlorella virus promoter or a mutant thereof can be cultured to generate stable transformants. Stable transformants can be generated by growth on medium that induces callus formation. Alternatively, confirmed transformants of haploid cell lines, such as the wheat cell line Pavon 64, can be doubled with colchicine or crossed with viable pollen to generate seeds.

Plants cells, calli or organs can also be transformed by Agrobacterium species carrying a binary $T_i$ vector including an expression cassette of the invention. The transformed plant cells, preferably tobacco or Arabidopsis, can form calli after plant cell growth on calli induction medium over a period of about 2 to 4 weeks. Plant organs, such as leaf, stem, hypococotyls, and cotyledons, can also be transformed by cocultivation with Agrobacterium species carrying binary $T_i$ vectors. Transformed plant organs can also be induced to form calli. The transformed calli are preferably grown in the presence of selective agents, such as antibiotics. After the transformed calli are formed and selected, the expression of the genes under control of a Chlorella virus promoter encoded by the first and/or second DNA sequence is detected. The transformed calli exhibit stable transformation. While not in any way meant to limit the invention, it is believed that replication and cell division in the formation of calli from the transformed plant cells or organ tissues, indicates that the expression cassette is stably integrated into the plant cell genome and is replicated and transmitted to progeny cells.

4. Formation of Transgenic Plants

The transformed plant calli exhibiting stable expression of the genes encoded by the first and/or second DNA sequence under the control of a Chlorella virus promoter or a mutant thereof can be used to generate transgenic plants. Methods of generating transgenic plants from calli are described in *Plant Molecular Biology Manual*, Kluwer Publishing (1988). Briefly, transformed plant cells are grown on callus or shoot induction medium containing a selective agent, typically an antibiotic until calli are formed, generally about 2–4 weeks. Transformed calli can be induced to form shoots in the presence of cytokinin in the medium. Transgenic plants can be regenerated after 4–6 weeks of incubation from shoot cultures.

Transgenic plants can be crossed with other transgenic and/or nontransgenic plants. The next ($F_1$) generation of plants can be examined for heritable transmission of an expression cassette of the invention. Transgenic progeny plants to which an expression cassette has been inheritably transmitted can provide transgenic seeds containing a heterologous gene under the control of a Chlorella virus promoter.

5. Method of Identifying Whether a Chlorella Virus Gene Promoter or Mutant Thereof Can Function to Express a Heterologous Reporter Gene The invention also provides a method for identifying whether a putative Chlorella virus gene promoter sequence or a mutant Chlorella virus gene promoter sequence can provide for gene expression of a heterologous gene. A heterologous gene is a gene different from the original or native Chlorella virus gene. The heterologous gene is preferably a promoterless reporter gene such as chloramphenicol acetyltransferase, β-galactosidase, β-glucuronidase, or human growth hormone.

In the method of the invention, a DNA fragment is isolated from a Chlorella virus gene. Once a Chlorella virus gene sequence has been cloned and identified, about 50 to 2000 nucleotide base pairs upstream from the 5' end of the coding sequence of the Chlorella virus gene can be isolated by restriction endonuclease digestion. This DNA fragment can then be operably linked to a heterologous gene to form an expression cassette.

An expression cassette can be formed by standard methodologies as described previously. Briefly, the DNA fragment encoding the putative promoter region or the mutant promoter region can be combined with the heterologous gene in a vector such as a plasmid as follows. A ColEI plasmid having multiple cloning sites can be digested with a restriction endonuclease specific for one of the sites. A heterologous gene such as the promoterless chloramphenicol acetyltransferase (CAT) is also digested with the same restriction endonuclease. The plasmid digest and the CAT gene are mixed and ligated with a ligase enzyme. The ColEI plasmids carrying the CAT gene are selected and amplified. These plasmids are then digested with a restriction endonuclease that cleaves at a multiple cloning site upstream from the newly inserted CAT gene. The DNA fragment containing putative Chlorella virus or mutant Chlorella virus promoter is mixed with the digested plasmid and ligated with ligase. Plasmids having the putative or mutant Chlorella virus promoter operably linked to the heterologous reporter gene, such as the gene encoding chloramphenicol acetyltransferase, are selected.

An expression cassette so formed is transformed into prokaryotic or eukaryotic host cells by standard methods. The standard methods include calcium coprecipitation, electroporation, biolistic transformation, and the like. The preferred transformed host cell is *E. coli*.

The expression of the heterologous gene can be detected by standard methods. Those methods include radiolabelled oligonucleotide probe hybridization to host cell mRNA, physical detection of the gene product and/or detection of the functional activity of the gene product. The detection of gene expression indicates that the putative or mutant promoter Chlorella virus gene sequence can function to provide expression of a heterologous gene.

In a preferred version, a putative or mutant promoter DNA sequence from a Chlorella virus DNA methyltransferase gene is combined with a promoterless reporter gene, such as the chloramphenicol acetyltransferase gene, in a ColEI plasmid. The ColEI plasmid is introduced into an *E. coli* host and the expression of the chloramphenicol acetyltransferase gene is evaluated. The expression of the chloramphenicol acetyltransferase gene is monitored by detecting the enzyme activity of chloramphenicol acetyltransferase in transformed cells.

EXAMPLE 1

Construction of a Vector Containing An Expression Cassette Including Promoters from Chlorella Virus DNA Methyltransferase Genes Fused with a Chloramphenicol Acetyltransferase Gene (CAT) Promoters A promoter of the invention is obtained or modified from a Chlorella virus gene. Chlorella viruses are large (150 to 190 nm) polyhedral plaque-forming viruses containing >300 kb of linear double-stranded DNA. At least 37 strains of the virus that infect eukaryotic Chlorella-like green algae have been isolated and partially characterized, as described in Van Etten et al., *Microb. Rev.*, 55:586 (1991). The viruses are placed into 16 classes on the basis of plaque size, antibody reactivity, and the nature and abundance of methylated bases in their genomic DNA. Each of the viral DNAs contains 5-methylcytosine at a percentage of cytosine ranging from 0.1% to 47.5%. In addition, 25 of the 37 viral DNAs also contain $N^6$-methyladenine as a percentage of adenine ranging from 1.45% to 37%. The finding of sequence specific methylation led to the discovery that these viruses have genes encoding DNA methyltransferases and site-specific endonucleases. In addition, these viruses contain at least 50 structural genes.

Some of the Chlorella virus genes, including the 5' flanking regions, have been isolated and sequenced. Four of the viral-encoded DNA methyltransferase genes have been isolated and sequenced, as reported by Shields et al., *Virology*, 176:16 (1990); Stefan et al., *Nucleic Acids Res.*, 19:307 (1991); Narva et al., *Nucleic Acids Res.*, 15:9807 (1987); and Zhang et al, *Nucleic Acid Research* (submitted for publication). Two DNA polymerase genes including 5' flanking regions from Chlorella viruses PBCV-1 and NY-2A were isolated and sequenced, as described by Grabherr et al., *Virology*, 188:721 (1992).

The gene encoding an adenyl methyltransferase including 5' and 3' flanking regions from Chlorella virus NC-1A was cloned into plasmid pUC8 and expressed in *E. coli* as described by Narva et al., cited supra. Briefly, virus NC-1A DNA was purified and a library of Sau3A partial digestion products of the NC-1A DNA was prepared in *E. coli* plasmid pUC8 by standard procedures, as described in Maniatis et al., *Molecular Cloning: A Laboratory Manual*, Cold Spring Harbor, N.Y. (1982). A clone containing the M.CviBIII gene, plasmid NC-1A.14.8 was selected from NC-1A DNA library by a procedure originally suggested by Mann et al., *Gene*, 3:97–112 (1978) to clone bacterial methyltransferase genes. The restriction endonucleases SalI (GTCGAC) and TaqI (TCGA) are inhibited by the presence of 6-methyldeoxyadenine in their recognition sequence. Since TCGA sequences are methylated by M.CviBIII, recombinant plasmids containing an M.CviBIII gene functional in *E. coli* are resistant to SalI and TaqI. These plasmids were selected by treating the plasmid library with SalI before transforming *E. coli*.

Several transformants of two SalI resistant clones were obtained when $10^5$ transforming units were digested before transformation of *E. coli* LE392. One clone, pNC-1A.14.8, contained a 2.1 kilobase pair (kbp) insert of NC-1A DNA and was resistant to SalI and TaqI when propagated in *E. coli*. A restriction endonuclease map of the 2.1 kbp fragment indicated a single NdeI site about 1.2 kbp from one end and no internal BamHI, BglIV, SstI, and HindIII sites. When Southern blots of NC-1A DNA digested with these restriction endonucleases were probed with nick-translated pNC-1A.14.8, two NdeI fragments and single BamHI, BglII, SstI, and HindIII fragments were identified as expected. Two fragments were also present in double digests of NdeI plus one of each of the other four restriction endonucleases. No hybridization to dot blots of host Chlorella NC64A DNA was observed. These results indicate that NC-1A Chlorella virus contains a single copy of the M.CviBIII gene and that the host Chlorella does not contain the gene.

The DNA sequence of the entire 2.1 kbp fragment containing the M.CviBIII gene was determined by dideoxynucleotide chain termination sequencing method and reported by Narva et al., cited supra. A single open reading frame (ORF) of 1131 base pairs (bp) was identified within the functional domain predicted by Tn5 mutagenesis which could encode a polypeptide of 377 amino acids with a molecular weight of 42,828. It was assumed that the ATG codon was the initiation codon for M.CviBIII for two reasons: (i) an ochre (TAA)' codon immediately precedes ATG, and (ii) fusion of the lacZ amino terminus at this site results in overproduction of M.CviBIII.

The Tn5 mutagenesis of recombinant plasmids, including pNC-1A.14.8, was performed as described by deBruijn et al., Gene, 27:131 (1984). Sites of Tn5 insertion within the M.CviBIII gene were mapped with HindIII and HindIII plus EcoRI. Insertional inactivation of the M.CviBIII gene was determined by testing the TaqI sensitivity of individual plasmids containing unique Tn5 elements.

An 851 bp putative promoter region present in the 5' flanking region of the M.CviBIII adenyl methyltransferase gene was subcloned into either ColEI plasmids or a binary $T_i$ vector. The plasmid NC-1A.14.8 containing the 2.1 kbp fragment was digested with HindIII and DraI to excise the 851 bp region. The promoter region so isolated was designated the AMT-1 promoter and was placed upstream of a promoterless chloramphenicol acetyltransferase (CAT) coding sequence in the ColEI plasmid or the binary $T_i$ vector by standard methods, as described in Sambrook et al., cited supra. The sequence of the 851 bp promoter designated AMT-1 is shown in Table I (SEQ ID NO: 1).

A second promoter region was obtained from digestion of the pNC-1A.14.8 with HindIII and XbaI. The second promoter fragment also contained the coding sequence for 53 amino terminal amino acids of the M.CviBIII methyltransferase protein. The second promoter construct was also subcloned upstream from the promoterless CAT coding sequence in ColEI plasmids or the binary $T_i$ vectors.

The adenine methyltransferase gene M.CviRI from Chlorella virus XZ-6E was cloned and sequenced as described by Stefan et al., cited supra. DNA libraries of EcoRI digestion products of Chlorella virus XZ-6E DNA were prepared in plasmid pBR322 and transformed in E. coli by standard methods (Maniatis et al., 1982).

Potential clones containing the M.CviRI and M.CviRII genes were selected from the XZ-6E DNA library. The restriction endonuclease PstI (CTGCAG) is inhibited by 6-methyladenine in the TGCA portion of its recognition sequence. Since M.CviRI methylates adenine in TGCA sequences, recombinant plasmids containing a M.CviRI gene which is expressed in E. coli are resistant to PstI. Likewise, clones containing M.CviRII were screened by treating the library with RsaI; RsaI cleaves GTAC but not GT$^m$AC sequences. Resistant plasmids were selected by treating the XZ-6E plasmid library with either PstI or RsaI before transforming E. coli.

About 100 transformants were obtained after PstI digestion of the partial EcoRI XZ-6E library. Plasmid DNA was isolated from 30 individual colonies and tested for resistance to PstI. One clone, named pXZ-6E5.9, contained a 5.9 kb insert of XZ-6E DNA and was resistant to PstI and CviRI. Plasmid pXZ-6E5.9 was sensitive to three other restriction endonucleases, RsaI, TaqI, and HinfI, whereas virus XZ-6E genomic DNA was resistant to each of these enzymes. It was concluded that pXZ-6E5.9 contains the M.CviRI gene.

Subclones of plasmid pXZ-6E5.9 were prepared and tested for sensitivity/resistance to PstI and CviRI. These experiments localized the M.CviRI gene to a 2.1 kb region at one end of pXZ-6E5.9; this plasmid was named pXZ-6E.14.

The entire viral insert DNA in plasmid pXZ-6E.14 was subcloned and sequenced as reported by Stefan, cited supra. Two open reading frames (ORF) of 243 (ORF-A) and 1137 bases were identified. These two ORFs could code for polypeptides of 81 (predicted molecular weight of 9,504) and 379 (predicted molecular weight of 42,814) amino acids, respectively. The larger ORF is the M.CviRI gene because the amino acid sequence is similar to other adenine methyltransferases.

The putative promoter region of about 610 bp located 5' to the potential start codon of the adenyl methyltransferase gene M.CviRI was subcloned into either ColEI plasmids or a binary $T_i$ vector. The plasmid pXZ-6E.14 containing a 2.1 kbp fragment was digested with restriction endonucleases XhoI and BglII to excise the 610 bp region. The promoter region so isolated was designated AMT-2 promoter and was placed upstream of a promoterless CAT coding sequence in the ColEI plasmid or the binary $T_i$ vector by standard methods. The DNA sequence of the AMT-2 promoter is shown in Table II (SEQ ID NO: 2).

The cytosine methyltransferase gene M.CviJI from Chlorella virus IL-3A was obtained as described in Shields et al., Virology, 176:16 (1990). Briefly, virus IL-3A DNA was purified and DNA libraries of Sau3A and TaqI partial digestion products of IL-3A DNA were prepared in E. coli plasmid pUC19 by standard methods (Maniatis et al., 1982).

Potential clones containing the M.CviJI gene were selected from the IL-3A DNA library by a procedure originally suggested by Mann et al., cited supra., to clone bacterial methyltransferase genes. The restriction endonucleases HindIII (AAGCTT) and SstI (GAGCTC) are inhibited by 5-methylcytosine in the AGCT portion of their recognition sequences. Since M.CviJI methylates cytosine in AGCT sequences, recombinant plasmids containing a functional M.CviJI gene should be resistant to HindIII and SstI. Resistant plasmids were selected by treating the IL-3A plasmid library with both HindIII and SstI before transforming E. coli.

Several transformants were obtained after HindIII and SstI digestion of partial Sau3A and TaqI IL-3A libraries. Plasmid DNA from nine colonies, all from the Sau3A library, were resistant to CviJI. These colonies had an insert DNA of about 10 kb or 7.2 kb. One of the latter colonies (named pIL-3A.22) was selected for detailed study. As expected, pIL-3A.22 DNA was also resistant to AluI and sensitive to other enzymes such as HhaI, ThaI and HpaII. The pIL-3A.22 contains the M.CviJI gene, however, the insert DNA also either contains a second cytosine methyltransferase gene or the M.CviJI enzyme is less specific than CviJI.

Subclones of plasmid pIL-3A.22 were prepared and tested for sensitivity to CviJI and HaeII. These experiments localize the M.CviJI gene and resistance to HaeII to a 3.7 kb region at the 3' end of pIL-3A.22. The M.CviJI gene was further defined by insertional mutagenesis of pIL-3A.22.8 with transposon Tn5. Plasmids containing Tn5 insertions were assayed qualitatively for M.CviJI directed methylation by testing the sensitivity of the plasmid DNAs to CviJI as well as HaeII. Independent insertions defined a region of 2 kb on pIL-3A.22.8 which could encode M.CviJI as well as resistance to HaeII.

The entire 3731 bp insert DNA from pIL-3A.22.8 was sequenced, as reported by Shields et al., cited supra. Three open reading frames of 483, 1101, and 486 bp which could code for polypeptides containing 161, 367, and 162 amino acids, respectively, were identified. The sequence of the 1101 bp plus flanking sequences is the M.CviJI because (i) it is the only ORF located in the region identified by Tn5 mutagenesis and (ii) it has amino acid motifs similar to those of other cytosine methyltransferases.

The 276 bp putative promoter contained within the 5' flanking region of the M.CviJI gene was subcloned upstream from the CAT coding sequence in either ColEI plasmids or binary $T_i$ vector. The plasmid pIL-3A.22.8 was digested with restriction endonuclease and the promoter region so isolated was designated CXT-1 promoter and was subcloned into the ColEI plasmid or binary $T_i$ vector by standard methods. The sequence of CMT-1 promoter is shown in Table III (SEQ ID NO: 3).

The putative promoter regions from the DNA methyltransferase genes were isolated and subcloned into ColEI or binary $T_i$ vectors by standard methods, as described by Sambrook et al. (1989). Briefly, the promoter DNA sequences of the methyltransferase genes and the ColEI or binary $T_i$ vectors were digested with restriction endonucleases and then ligated with $T_4$ DNA ligase. The resulting plasmids carrying the putative promoter regions from the Chlorella virus methyltransferase genes were selected and amplified in *E. coli* MC1000.

The ColEI plasmids pUC18 and pUC19 are well characterized plasmids described in Yanisch-Perron et al., cited supra, an can be obtained from Strategene or New England Biolabs. The chloramphenicol acetyltransferase gene is a well known reporter gene and was obtained in plasmid pSVOCAT, as described in Gorman et al., *Mol. Cell Biol.*, 2:1044–1051 (1982). The chloramphenicol acetyltransferase gene coding sequence lacking native promoter sequence was subcloned into the ColEI plasmid and the binary $T_i$ vector by standard methods, as described by Sambrook et al., cited supra.

The binary $T_i$ plasmid vector pGA582 was obtained as follows. A binary $T_i$ vector for plant transformation and promoter analysis was formed as described by An, *Methods in Enzymology*, 153:292 (1987). Binary vectors can be manipulated in *E. coli* and then transferred and maintained in Agrobacterium. The plasmid pGA582 is a 13.2 kbp long binary vector and is available from Dr. An or Dr. Mitra. The plasmid has DNA fragments (about 700 bp) containing the nopaline T-DNA right border and a fragment (600 bp) containing the nopaline T-DNA left border. There are nine unique restriction sites in the T-DNA borders for cloning foreign DNA. These are HindIII, XbaI, SacI, HbaI, KpnI, ClaI, BglII, ScaI, and EcoRI. The first seven sites are clustered in multiple cloning sites. The vector also contains the ColEI origin of replication. The pGA582 also carries a wide host range replicon and tetracycline resistance gene allowing for stable maintenance of the plasmid in *E. coli* and Agrobacterium. The promoterless chloramphenicol acetyltransferase gene was inserted in place of the 2.7 kb BglII EcoRI endonuclease fragment containing the ColEI replication and cos site.

The 1.5 kbp DNA sequence inserted in that site contains the CAT gene as well as the plant terminator sequence derived from octopine T-DNA transcripts. The putative promoter sequences from the Chlorella virus DNA methyltransferase genes were inserted upstream from the promoterless CAT gene in one of the multiple cloning sites.

EXAMPLE 2

Transfer and Expression of Chlorella Virus Promoter-CAT Constructs Into Prokaryotic and Host Cells The ColEI plasmids or the binary $T_i$ vectors containing either the AMT-1, AMT-2, the 5' deleted AMT-1, or the CMT-1 promoters fused to the chloramphenicol acetyltransferase (CAT) gene were introduced into eukaryotic and prokaryotic host cells, and the expression of chloramphenicol acetyltransferase was measured.

Prokaryotic host cells selected were *E. coli*, phytopathogenic members of the genera Pseudomonas and Erwinia, and Agrobacterium. ColEI plasmids or the binary $T_i$ vectors carrying the Chlorella virus promoter-CAT constructs were introduced into bacteria by the calcium coprecipitation method or by the electroporation method. Transformed bacteria carrying promoter-CAT constructs were selected in the presence of ampicillin or tetracycline. The presence of plasmid DNA containing the Chlorella virus promoter-CAT constructs in the selected bacteria was verified by alkaline lysis DNA miniprep method, as described in Sambrook et al., cited supra.

Gene expression in the transformed cells was measured by quantitating the activity of the gene product of the chloramphenicol acetyltransferase gene after 24–48 hours of culture. The expression pattern of the AMT-CAT constructs was, in some cases, compared to the expression of the 35S promoter from cauliflower mosaic virus fused to the chloramphenicol acetyltransferase gene.

Chloramphenicol acetyltransferase is assayed in cell extracts in the following reaction mixture: 10–20 ml of cell extract, 100 ml of 0.25 M Tris-HMl pH=7.8, 10 ml of 4 mM acetyl coenzyme A, 50 MCi of [$^{14}$C] chloramphenicol (57 mCi/mmol, New England Nuclear). The mixture was incubated at 37° C. for 20 minutes. The reaction was stopped by adding 1 ml of ethylacetate. The mixture was centrifuged and the ethylacetate was removed by evaporation to dryness. The dried pellet was dissolved in 30 ml of ethylacetate and run on silica gel thin-layer chromatography (TLC). The TLC plate was run in 95% chloroform/5% methanol. An X-ray film was exposed to the chromogram overnight and the film developed. Radioactive spots migrating with an Rf similar to the standard were detected.

Plasmid pAM-55 was constructed from pGA582 plasmid and contains the neomycin phosphotransferase gene and tetracycline resistance gene, as described in Mitra and An, *Mol. Gen. Genetics*, cited supra. The promoterless CAT gene was subcloned into BamHI restriction endonuclease site. The Chlorella virus promoter sequences were not fused with the promoterless CAT gene. This plasmid was used to determine whether the CAT structural gene could be driven by any other promoter on the plasmid. *E. coli* MC1000 was transformed with pAM-55 by the calcium coprecipitation method. No CAT activity was detected in the transformed cells indicating that promoterless CAT gene subcloned into ColEI plasmids was not expressed without the Chlorella virus or 35S cauliflower mosaic virus promoters.

The pAM-15 plasmid was constructed in a ColEI plasmid and contains AMT-CAT fused DNA constructs as well as a gene encoding resistance against ampicillin. Two of plasmid DNA was used to transform bacterial cells by the calcium coprecipitation method. The bacteria transformed were *E. coli* and phytopathogenic bacteria from the genera Erwinia and Bacillus. The results are shown in FIG. 1. Lane 1 corresponds to *E. coli* MC1000; Lane 2 corresponds to *E. coli* JN83; Lane 3 corresponds to *Bacillus pumulis*; Lane 4 corresponds to *Erwinia amylovora*; and Lane 5 corresponds to *Erwinia carotovora*; P corresponds to positive CAT control; and N corresponds to negative CAT control.

The results show that the AMT-1 promoter provided for high level of constitutive expression of the chloramphenicol acetyltransferase gene in *E. coli* and in some phytopathogenic species of Erwinia. No expression was detected in *Bacillus pumulis*.

The pAM-50 plasmid was constructed from pGA582 plasmid, and contained the neomycin phosphotransferase gene and tetracycline resistance gene. The Chlorella virus AMT promoter fused to CAT construct was also present. Two μg of plasmid DNA was used to transform bacterial cells by electroporation. The results are shown in FIG. 2. The bacterial cells include *Clavibacter michiganense* ssp. Nebraskense (Lane 1); *Pseudomonas syringae* pv. *syringae* (Lane 2); *Xanthomonas campestris* pv. *asclepiadis* (Lane 3);

and *Agrobacterium tumefaciens* (Lane 4). The positive CAT control is shown in Lane 5 and the negative control in Lane 6.

The results show that the Chlorella virus AMT promoter can be expressed in a phytopathogenic bacterial species *Pseudomonas syringae* pv. *syringae*, as well as *Agrobacterium tumefaciens*. Thus, the AMT promoter is functional in a wide variety of bacterial species, making this promoter useful in cloning and expressing heterologous genes in different bacterial species.

EXAMPLE 3

Analysis of Promoter Activity of AMT-5' Deletion Mutants

Promoters have regulatory regions that are essential to regulate levels of expression and tissue-specific expression. Mutations of promoter regions can significantly change promoter function, including tissue-specific promoter expression patterns. Mutant promoter DNA sequences can be obtained by known methods of deletion mutagenesis, insertional mutagenesis, or site-specific mutagenesis, or combinations thereof as described by Lam et al., *PNAS*, 86:7890 (1989) and Ha et al., *PNAS*, 85:8017 (1988).

Promoter region deletion mutants were generated as described by Ha et al., cited supra. Plasmids pUC18 and pUC19 are plasmids that are obtained and have the characteristics as described by Yanisch-Perron et al., *Gene*, 33:103 (1985) (SEQ ID NO: 4). A synthetic nucleotide (GGTACCTCGAGGCCT) containing restriction sites for KpnI, XhoI, StuI was inserted into pUC18 and pUC19 plasmids in a unique SspI site upstream of the β-lactamase gene. The SmaI-DraI fragment containing the AMT-1 promoter region of the adenyl methyltransferase gene was then inserted into the HindIII site within the LacZ α-complementation gene of the pUC18 and pUC19 plasmids. The plasmids were the starting materials for generating 5' and 3' deletion mutants.

The resulting plasmids were linearized with HindIII and digested with an exonuclease, BAL-31, in solution (600 mM NaCl/12 mM $CaCl_2$/12 mM $MgCl_2$/20 mM Tris-HCl, pH=8.0) at 30° C. The reaction was stopped at 1-minute intervals by removing a portion of the mixture and adding it into an Eppendorf test tube containing 0.1 ml of a 0.3 M sodium acetate (pH=7.0), 0.1 ml chloroform, and 0.1 ml phenol. After mixing vigorously, the test tube was centrifuged for 2 minutes and the aqueous phase was precipitated with 2 vol of ethanol. DNA was dissolved in 10 ml of medium-salt buffer (50 mM NaCl/10 mM $MgCl_2$/50 mM Tris-HCl, pH=8.0), digested with StuI, and self-ligated with T4 DNA ligase. Ligated DNA was introduced into *E. coli* MC1000 and the 5' deletion mutants were analyzed by digesting DNA prepared from the ampicillin resistant colonies with XhoI and HindIII. The 3' deletion mutants can be generated in a similar manner but by placing the synthetic oligonucleotide linker downstream from the promoter region.

Using these methods, three 5' deletion mutants were isolated and characterized. The deletion end points were determined by the Maxam-Gilbert DNA sequencing method after labelling the deletion end point with [$\alpha^{32}P$] dGTP and DNA polymerase large fragment. The 5' deletion mutants generated were lacking 304, 529 and 753 nucleotide base pairs from the 5' end of the AMT-1 promoter. The 5' deletion mutants were then fused with the CAT gene and subcloned into ColEI plasmids or the $T_i$ binary vectors, as described previously.

The three 5' deletion mutants of the AMT promoter were used to transform competent *E. coli* cells by the calcium coprecipitation method and analyzed for CAT activity. The results are shown in FIG. 3.

The deletion endpoints of the 5' deletion mutants are shown to the left. The deletion end points are measured from the translational start codon. The first nucleotide to the left of the start codon is designated −1. The AMT promoter mutants lacking 304 nucleotides from the 5' end of the AMT-1 promoter were functional in *E. coli*. The AMT promoter mutants lacking 529 nucleotides (−325) and 753 nucleotides (−101) did not provide for CAT expression in *E. coli*.

The same 5' deletion mutants of the AMT promoter were also evaluated for expression in tobacco calli. Suspension culture tobacco cells were transformed with 5' deletion mutants and transformed calli were analyzed for CAT activity. The results indicate that only the full length promoter (−851) was functional in tobacco calli.

The analysis of the 5' deletion mutants indicates that for some hosts removal of a portion of the AMT-1 promoter sequence did not impair the function of the promoter. The expression of one of the 5' deletion mutants (−550) in *E. coli* and not in tobacco cells suggests that mutants of the AMT promoters can be generated that are selectively expressed in certain host cell types.

EXAMPLE 4

Stable and Transient Expression of Chlorella Virus Promoters in Eukaryotic and Prokaryotic Cells Plasmids containing the AMT-CAT expression cassette were used to transform rice, wheat, tobacco, and Arabidopsis cells. Tobacco and Arabidopsis cells were cultured for the development of transformed calli. The expression of CAT driven by the AMT promoters was compared to the expression of CAT driven by the 35S promoter from cauliflower mosaic virus (CaMV). Transient expression of CAT was measured after 24–48 hours of culture of the transformed cells. Stable expression of CAT was measured in tobacco and Arabidopsis calli, *Agrobacterium tumefaciens*, and *E. coli*.

Wheat, rice and tobacco cells were transformed with plasmids containing the AMT-CAT expression cassette or the 35S CaMV promoter-CAT expression cassette. ColEI plasmids containing the expression cassettes were introduced into the plant cells by electroporation. Transient CAT activity was measured in the transformed plant cells after 24–48 hours. The results are shown in FIG. 4.

The AMT promoter provided for a high level of transient expression in wheat, rice and tobacco cells. The level of expression was higher than that seen with the 35S CaMV promoter-CAT constructs. Similar experiments were done with the CMT-1 promoter-CAT expression cassette and the results also indicated that the CMT-1 promoter could function to provide for gene expression in the plant cells (data not shown).

For analysis of stable transformation, tobacco and Arabidopsis cells were transformed with Agrobacterium carrying a binary $T_i$ vector and cultured for the development of calli. *Agrobacterium tumefaciens* was transformed using the binary $T_i$ vectors carrying the Chlorella virus AMT-promoter fused to CAT or the 35S CaMV promoter fused to CAT. Tobacco leaf discs and Arabidopsis cells were cocultivated with Agrobacterium carrying the binary $T_i$ vectors.

After cocultivation for two days at 28° C., the bacterial cells were washed out and the tobacco leaf discs and Arabidopsis cells were grown on callus induction medium containing 200 μg of kanamycin and 250 μg/ml of carbenicillin. The cocultivated plant tissues were incubated in the dark for callus induction.

Once transformed tobacco and Arabidopsis calli were formed and selected, expression of the AMT-CAT constructs was measured in plant extracts as described in Example 2. Plant extracts were obtained by lysis of calli with a pestle or by sonication in plant extraction buffer (0.5 molar sucrose, 0.1% ascorbic acid, 0.1% cysteine-HCl, 0.1 molar Tris-HCl, pH=7.8). The lysate was centrifuged and the supernatant assayed for chloramphenicol acetyltransferase. The results are shown in FIG. 4.

The results in FIG. 4 show that in both transformed tobacco and Arabidopsis calli, the AMT promoter chloramphenicol acetyltransferase fused gene was strongly expressed. The levels of expression were greater than that of the 35S cauliflower mosaic virus chloramphenicol acetyltransferase constructs. Thus, the AMT promoter provides for high level of transient as well as stable gene expression.

Tobacco and Arabidopsis calli transformed with an expression cassette containing Chlorella virus AMT promoter fused to CAT were used to regenerate transformed plants. The transformed or transgenic plants, as well as the F1 generation of the transformed plants were analyzed for CAT expression. Both transformed plants and the F1 generation exhibited strong expression of the chloramphenicol acetyltransferase gene indicating that the AMT promoter-CAT constructs can be stably transmitted and expressed from generation to generation.

EXAMPLE 5

Formation of Chlorella Virus AMT-Neomycin Phosphotransferase Gene and Hygromycin Resistant Gene Expression Cassettes and Transformation of Wheat The AMT promoters were combined with promoterless chloramphenicol acetyltransferase (CAT) gene, as described in the previous Examples. The expression of this "reporter" gene allowed for a standardized measurement of gene expression in a variety of cell types. The AMT promoters were also combined with genes known to be plant selectable markers. One of the genes is known as neomycin phosphotransferase gene II and is known to encode resistance of plant cells to G-418.

The neomycin phosphotransferase gene is present in the binary $T_i$ vector obtained as described in Example 1. A promoterless neomycin phosphotransferase gene was obtained by restriction endonuclease digestion of the pGA582 plasmid and inserted downstream from the AMT promoter in the ColEI plasmid by standard methods. Likewise, a promoterless hygromycin resistance gene can be subcloned into the ColEI plasmid downstream from the AMT promoter using standard methods provided in Sambrook et al., cited supra.

The haploid wheat cell line, Pavon 64, was transformed with the fused AMT promoter-neomycin phosphotransferase gene. Pavon 64 calli were partially treated with 0.1% pectolyase Y-23 and 1% cellulase RS. The cells were electroporated with 25 μg of plasmid ColEI DNA and 75 μg carrier DNA at 400 volts with a capacitance of 800 μF. The electroporated cells were grown on 85D12 regeneration medium without any plant growth regulators as described by Liang et al., *Crop Sci.*, 27:336 (1987).

Transformed cells were assayed for neomycin phosphotransferase activity to detect expression of neomycin phosphotransferase gene. Neomycin phosphotransferase was assayed by standard methods. Briefly, 10 μl of plant extract, 10 μl of assay buffer (40 mM magnesium chloride, 40 mM ammonium chloride, 2 mM dithiothreotal, 65 mM Tris-HCl, pH=7.5), 2 μl of Kanamycin sulfate and 10 μl of ATP solution (50 μM ATP and 0.1 mCi [$^{32}$p] ATP, 3000 Ci/mmol) was mixed and incubated for 20 minutes at 37° C. The solution was spotted onto 1 cm$^2$ of Whatman P-81 phosphocellulose paper and dried under a heat lamp. The spotted Whatman paper was washed and then counted in a scintillation counter.

The results of transformation of the wheat cell line with the AMT-neomycin phosphotransferase expression cassettes show that transient gene expression was obtained in the embroyides 36 hours after the electroporation. Thus, the wheat cells were transformed and could express the neomycin phosphotransferase gene under the control of the Chlorella virus AMT promoters.

Stable transformation of wheat plants will be tested by the following method. Hygromycin or Kanamycin resistant transgenic wheat plants will be doubled with colchicine or crossed with viable pollen to produce seeds as described in Liang et al., *Crop. Sci.*, 27:336–339 (1987). Seeds will be grown and the F1 plants tested for neomycin phosphotransferase gene expression or hygromycin resistance.

The references are incorporated by reference. The invention has been described with reference to various specific and preferred embodiments and techniques. However, it should be understood that many variations and modifications may be made while remaining within the spirit and scope of the invention.

What is claimed is:

1. An expression cassette comprising a promoter or a mutant thereof substantially corresponding to a promoter from a Chlorella virus DNA methyltransferase gene operably linked to a first DNA sequence encoding a gene that is different from the Chlorella virus gene.

2. An expression cassette of claim 1 further comprising a 3' nontranslated regulatory DNA sequence operably linked to the first DNA sequence, wherein the 3' nontranslated regulatory DNA sequence has a polyadenylation sequence and functions in eukaryotic cells.

3. An expression cassette of claim 1 further comprising a second DNA sequence linked to the first DNA sequence, the second DNA sequence encoding a different gene from the first DNA sequence and from the Chlorella virus DNA methyltransferase gene.

4. An expression cassette of claim 3 further comprising a 3' nontranslated regulatory DNA sequence operably linked to the second DNA sequence, wherein the 3' nontranslated regulatory DNA sequence has a polyadenylation sequence and functions in eukaryotic cells.

5. An expression cassette of claim 2, wherein the promoter substantially corresponds to the promoter from an adenyl methyltransferase gene from Chlorella virus NC-1A.

6. An expression cassette of claim 2, wherein the promoter substantially corresponds to the promoter from a cytosine methyltransferase gene from Chlorella virus IL-3A.

7. An expression cassette of claim 2, wherein the promoter substantially corresponds to the promoter from an adenyl methyltransferase gene from Chlorella virus X2-6E.

8. An expression cassette of claim 1, wherein the promoter is the AMT-1 promoter.

9. The promoter according to claim 1, wherein the promoter is the AMT-2 promoter.

10. The promoter according to claim 1, wherein the promoter is the CMT-1 promoter.

11. An expression cassette of claim 1, wherein the promoter is an AMT-1 promoter with about 1 to about 304 nucleotides deleted from the 5' end of the promoter.

12. An expression cassette of claim 1, wherein the promoter comprises from about 3 to about 150 nucleotides of the coding sequence of the Chlorella virus gene.

13. An expression cassette of claim 1, wherein the promoter is a deletion mutant.

14. A plasmid comprising the expression cassette of claim 1.

15. A plasmid of claim 14, wherein the plasmid is a binary $T_i$ vector.

16. An expression cassette of claim 1, wherein the first DNA sequence codes for a gene product selected from the group consisting of chloramphenicol acetyltransferase, neomycin phosphotransferase, a gene product conferring hygromycin resistance, β-glucuronidase, 5-enol-pyruvyl-phosphoshikimate synthase, octopine synthase, nopaline synthase, Bacillus thuringiensis toxin, a gene product conferring chlorsulfuron resistance, and a gene product conferring sulfmetron resistance.

17. An expression cassette of claim 3 wherein the second DNA sequence encodes a selectable marker gene selected from the group consisting of neomycin phosphotransferase gene, apramycin resistance gene, hygromycin β-phosphotransferase gene, dihydrofolate reductase gene, guanine phosphoribosyl transferase gene, hypoxanthine phosphoribosyl transferase gene, and thymidine kinase gene.

18. An expression cassette of claim 2, wherein the 3' nontranslated regulatory DNA sequence functions in plant cells.

19. An expression cassette of claim 2, wherein the 3' nontranslated regulatory DNA sequence substantially corresponds to the 3' flanking nucleotides of the octopine synthase gene.

20. The plasmid of claim 15 having the characteristics of plasmid pAM-15, ATCC No. 69069.

21. A transformed plant cell that contains an expression cassette comprising a promoter or mutant thereof substantially corresponding to a promoter from a Chlorella virus DNA methyltransferase gene operably linked to;
   a first DNA sequence encoding a gene that is different from the Chlorella virus gene; and
   a 3' nontranslated regulatory DNA sequence operably linked to the first DNA sequence, wherein the 3' nontranslated regulatory DNA sequence has a polyadenylation sequence and functions in plant cells.

22. A transformed plant cell of claim 21 having an expression cassette comprising a Chlorella virus DNA methyltransferase gene promoter selected from the group consisting of AMT-1 promoter, AMT-2 promoter, CMT-1 promoter, and AMT-1 promoter with about 1 to about 304 nucleotides deleted from the 5'-end of SEQ ID NO: 1; the promoter being operably linked to:
   a first DNA sequence encoding a gene product that is different from the Chlorella virus gene; and
   a 3' nontranslated regulatory DNA sequence operably linked to the first DNA sequence, wherein the 3' nontranslated regulatory DNA sequence has a polyadenylation sequence and functions in plant cells, wherein the promoter functions in eukaryotic or prokaryotic cells.

23. A plant cell of claim 21 further comprising a second DNA sequence linked to the first DNA sequence, wherein the second DNA sequence encodes a different gene product from the first DNA sequence and from the Chlorella virus DNA methyltransferase gene product.

24. A transgenic plant comprising plant cells having an expression cassette stably integrated into the genome, the expression cassette comprising a promoter substantially corresponding to a promoter from a Chlorella virus DNA methyltransferase gene or a mutant thereof operably linked to:
   a first DNA sequence encoding a gene that is different from the Chlorella virus DNA methyltransferase gene; and
   a 3' nontranslated regulatory DNA sequence operably linked to the first DNA sequence, wherein the 3' nontranslated regulatory DNA sequence has a polyadenylation signal and functions in plant cells.

25. A seed comprising a transformed plant cell of claim 24.

26. A transgenic plant according to claim 24 wherein the plant cells are obtained from monocotyledonous plants.

27. A transgenic plant according to claim 24, wherein the plant cells are wheat cells.

28. A transformed plant cell according to claim 21, wherein the plant cell is obtained from monocotyledonous plants.

29. A transformed plant cell according to claim 28, wherein the plant cell is a wheat cell.

30. A transformed bacterial cell that contains an expression cassette comprising: a promoter or mutant thereof substantially corresponding to a promoter from a Chlorella virus DNA methyltransferase gene operably linked to; a first DNA sequence encoding a gene that is different from the Chlorella virus DNA methyltransferase gene.

31. A transformed bacterial cell of claim 30, said cell comprising a bacterial cell selected from the group consisting of Agrobacteria or *E. coli* that contains an expression cassette comprising a Chlorella virus DNA methyltransferase gene promoter selected from the group consisting of AMT-1 promoter, AMT-2 promoter, CMT-1 promoter and AMT-1 promoter with about 1 to about 304 nucleotides deleted from the 5'-end of SEQ ID NO: 1; the promoter being operably linked to a first DNA sequence encoding a gene product that is different from the Chlorella virus DNA methyltransferase gene, wherein the promoter functions in a prokaryotic or eukaryotic cell.

32. A bacterial cell according to claim 30, wherein the bacteria is a phytopathogenic bacteria.

33. A bacterial cell of claim 32, wherein the bacterial cell is a member of the genus Pseudomonas.

34. An isolated promoter that substantially corresponds to a promoter of a Chlorella virus DNA methyltransferase gene.

35. The isolated promoter according to claim 34 that substantially corresponds to the AMT-1 promoter.

36. The isolated promoter according to claim 34 that substantially corresponds to the AMT-2 promoter.

37. The isolated promoter according to claim 34 that substantially corresponds to the CMT-1 promoter.

38. A method of producing a recombinant gene product in a cell, comprising:
   (a) forming an expression cassette wherein the expression cassette comprises a promoter from a Chlorella virus DNA methyltransferase gene operably linked to a first DNA sequence encoding a gene that is different from the Chlorella virus DNA methyltransferase gene, and wherein the promoter causes expression of the first DNA sequence in prokaryotic or eukaryotic cells; and
   (b) stably transforming a cell with the expression cassette.

39. The method of claim 38, comprising:
   (a) forming an expression cassette wherein the expression cassette comprises a Chlorella virus DNA methyltransferase gene promoter selected from the group consisting of AMT-1 promoter, AMT-2 promoter, CMT-1 promoter, and AMT-1 promoter, with about 1 to about 304 nuclebtides deleted from the 5'-end of SEQ ID NO: 1; the promoter being operably linked to a first DNA sequence encoding a gene product that is different from the Chlorella virus DNA methyltransferase gene product, and wherein the promoter causes expression of the first DNA sequence in prokaryotic or eukaryotic cells;

(b) stably transforming a cell to include the expression cassette; and (c) causing the cell to produce the recombinant gene product.

40. The method according to claim 38, wherein the promoter is the AMT-1, AMT-2, or CMT-1 promoter.

41. The method according to claim 38, wherein the expression cassette further comprises a second DNA sequence operably linked to the first DNA sequence, wherein the second DNA sequence is different from the first DNA sequence and the Chlorella virus DNA methyltransferase gene.

42. The method according to claim 38, wherein the cell is a bacterial cell.

43. The method according to claim 40, wherein the cell is a prokaryotic cell.

44. An isolated promoter of claims 35 comprising a DNA sequence corresponding to SEQ ID NO:1.

45. An isolated promoter of claim 36 comprising a DNA sequence corresponding to SEQ ID NO:2.

46. An isolated promoter of claim 37 comprising a DNA sequence corresponding to SEQ ID NO:3.

47. An expression cassette of claim 1, wherein the expression cassette further comprises a portion of the coding sequence of the Chlorella virus gene.

48. An expression cassette of claim 1 wherein the promoter causes expression of the first DNA sequence in bacteria or plant cells.

49. An expression cassette of claim 3 wherein the promoter causes expression of the first DNA sequence in bacteria or plant cells.

* * * * *